(12) United States Patent
Akechi et al.

(10) Patent No.: US 10,029,253 B2
(45) Date of Patent: Jul. 24, 2018

(54) MICRO DROPLET OPERATION DEVICE AND REACTION PROCESSING METHOD USING THE SAME

(71) Applicant: SHIMADZU CORPORATION, Kyoto-shi, Kyoto (JP)

(72) Inventors: Masakazu Akechi, Kyoto (JP); Masaki Kanai, Kyoto (JP); Takahiro Nishimoto, Kyoto (JP); Nobuhiro Hanafusa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 985 days.

(21) Appl. No.: 14/052,299

(22) Filed: Oct. 11, 2013

(65) Prior Publication Data

US 2014/0051160 A1 Feb. 20, 2014

Related U.S. Application Data

(62) Division of application No. 12/746,749, filed as application No. PCT/JP2007/073774 on Dec. 10, 2007, now Pat. No. 8,568,668.

(51) Int. Cl.
*B01L 3/00* (2006.01)
*C12M 1/32* (2006.01)
(Continued)

(52) U.S. Cl.
CPC ....... *B01L 3/502715* (2013.01); *B01L 3/5027* (2013.01); *B01L 3/502723* (2013.01);
(Continued)

(58) Field of Classification Search
CPC ........... B01L 3/502723; B01L 3/50273; B01L 3/502746; B01L 3/50853
See application file for complete search history.

(56) References Cited

U.S. PATENT DOCUMENTS 4,956,150 A 9/1990 Henry
6,004,515 A 12/1999 Parce et al.
(Continued)

FOREIGN PATENT DOCUMENTS

JP 2004-163104 A 6/2004
JP 2005-114430 A 4/2005
(Continued)

OTHER PUBLICATIONS

International Search Report for the Application No. PCT/JP2007/073774 dated Mar. 18, 2008.
(Continued)

*Primary Examiner* — Jan Ludlow
(74) *Attorney, Agent, or Firm* — Cheng Law Group, PLLC

(57) ABSTRACT

Micro droplets are accurately placed in a reaction well. The reaction well (5) is formed in one surface of a well base (3). A channel base (11) is placed on the well base (3). The channel base (11) has, in its surface joined to the well base (3), a liquid introduction channel (12a) and a reaction well air vent channel (18a). The channel base (11) also has a recess (27) formed opposite to the reaction well (5) and recessed upward from the upper surface of the liquid introduction channel (12a). When viewed from above, a shoulder part (26) of the recess (27) is placed near the connection part between the reaction well (5) and the liquid introduction channel (12a) and is closer to the center of the reaction well (5) than a shoulder part (16) of the reaction well (5).

3 Claims, 22 Drawing Sheets

(51) Int. Cl.
G01N 35/00 (2006.01)
G01N 35/10 (2006.01)

(52) U.S. Cl.
CPC ....... *B01L 3/502746* (2013.01); *C12M 23/12* (2013.01); *B01L 3/502738* (2013.01); *B01L 2200/027* (2013.01); *B01L 2200/0605* (2013.01); *B01L 2200/0642* (2013.01); *B01L 2300/04* (2013.01); *B01L 2300/046* (2013.01); *B01L 2300/0816* (2013.01); *B01L 2300/0858* (2013.01); *B01L 2300/0861* (2013.01); *B01L 2300/0864* (2013.01); *B01L 2300/0887* (2013.01); *B01L 2400/0622* (2013.01); *B01L 2400/0644* (2013.01); *B01L 2400/084* (2013.01); *G01N 2035/00158* (2013.01); *G01N 2035/1034* (2013.01)

(56) References Cited

U.S. PATENT DOCUMENTS

| | | | | |
|---|---|---|---|---|
| 6,391,578 | B2* | 5/2002 | Williams | ............. B01L 3/5085 435/288.3 |
| 7,560,073 | B1 | 7/2009 | Peters et al. | |
| 8,337,777 | B2 | 12/2012 | Nurse et al. | |
| 2001/0036669 | A1* | 11/2001 | Jedrzejewski | ....... B01J 19/0046 436/94 |
| 2004/0084402 | A1* | 5/2004 | Ashmead | ............ B01L 3/50273 216/27 |
| 2007/0014695 | A1* | 1/2007 | Yue | .................. B01L 3/502707 422/400 |
| 2009/0218704 | A1 | 9/2009 | Murakami | |

FOREIGN PATENT DOCUMENTS

| | | |
|---|---|---|
| JP | 2005-177749 A | 7/2005 |
| JP | 2006-177850 A | 7/2006 |
| JP | 2006-349557 A | 12/2006 |
| JP | 2007-114162 A | 5/2007 |
| WO | WO-99/46045 A1 | 9/1999 |
| WO | WO-2007/125642 A1 | 11/2007 |

OTHER PUBLICATIONS

Kanai, Masaki et al., "A Multi Cellular Diagnostic Device for High-Throughput Analysis", Proceeding of MicroTAS2004 (8th International Conference on Miniaturized Systems for Chemistry and Life Sciences), Sep. 2004, pp. 126-128.

* cited by examiner (A1) 
(B1)

(A2) 
(B2)

(A3) 
(B3)

(A4) 
(B4)

MICRO DROPLET OPERATION DEVICE AND REACTION PROCESSING METHOD USING THE SAME

CROSS REFERENCE TO RELATED APPLICATIONS

This application is a Divisional application of patent application Ser. No. 12/746,749, filed on Aug. 10, 2010 which is a 371 application of Application No. PCT/JP2007/073774, filed Dec. 10, 2007, the entire contents of which are hereby incorporated by reference.

BACKGROUND OF THE INVENTION

1. Field of the Invention

The present invention relates to organic chemistry in which organics are synthesized in minute amounts of samples and biochemistry in which a. PCR (polymerase chain reaction) method or the like is conducted, particularly to a microchip (µTAS: Micro Total Analysis System) into which functions of analyzing components of liquids, pretreatment functions, and the like are integrated, and also to a reaction processing method.

2. Description of the Related Art

Micro multi-chamber devices are used as small reactors used for biochemical analysis and usual chemical analysis. Such devices use, for example, microwell reaction well plates such as microtiter plates in which a plurality of well are formed as reaction wells in a planar plate surface (see Japanese Patent Laid-Open No. 2005-177749).

When a minute amount of a liquid sample is handled, sampling of the liquid sample or sample addition is typically performed using a micropipettor.

In that case, since the sample reaction site is open, there is a fear that a foreign matter may be mixed into the sample from outside. Moreover, the sample might contaminate the outside environment. It is desired that a sample be treated in the device to prevent a foreign matter from mixing from the outside and prevent outside environmental pollution.

In addition, it is desirable to increase the number of reaction wells that are integrated in the plate surface to further improve the efficiency of analysis using such a micro reactor. However, when the number of reaction well is increased, it is difficult to equally distribute samples into each reaction well.

Hence, the present inventors propose a passive sample Introduction method in which a plurality of reaction wells are formed in a base body and liquid samples can be equally dispensed thereinto (see M. Kanai, et. al. "A Multi Cellular Diagnostic Device for High-throughput Analysis", Proceeding of µTAS2004, pp. 126-128, 2004). The word "passive sample introduction method" means that a liquid sample flowing in a channel is dispensed by branching the channel stepwise without giving force or energy interacting with the liquid sample flowing in the channel to the sample from the outside.

Additionally, a structure of weighing out a small amount of a liquid that can quantitatively treat a small amount of a liquid is provided. The structure includes a first channel, a second channel, a third channel opened in the channel wall of the first channel, and a fourth channel opened in the channel wall of the second channel, connecting one end of the third channel to the second channel and weakening capillary attraction thereon as compared with the third channel (see, e.g., Japanese Patent Laid-Open No 2004-163104 and Japanese Patent Laid-Open No. 2005-114430).

According to the structure of weighing out a small amount of a liquid, a liquid introduced into the first channel is drawn into the third channel. Then the liquid remaining in the first channel is removed, and a liquid of a volume corresponding to the volume of the third channel can be weighing out by the second channel.

However, when a small amount of a liquid sample is transferred to a reaction well and the amount of the liquid sample is as minute as 10 µL (microliter) or less, once the liquid sample is contacted with the ceiling of the reaction well (plate surface disposed opposite to the reaction well), the weight of the liquid droplet is so small that the droplet cannot fall by gravitation, whereby the liquid sample may remain sticked to the ceiling of the reaction well without falling.

FIG. 24 is a schematic sectional view that shows a conventional micro droplet operation device. FIG. 24 shows a state when a liquid sample 30 is injected into a reaction well 5 from a liquid introduction channel 12a formed between a base plate 3 and a cover plate 11. As shown in FIG. 24, when the weight of the liquid sample 30 is very small, a droplet of the liquid sample 30 attaches to a side wall or the ceiling of the reaction well 5 and thus the sample may not sufficiently react with a reagent (not shown) present at the bottom of the reaction well 5.

SUMMARY OF THE INVENTION

Hence, an object of the present invention is to provide a micro droplet operation device capable of precisely injecting a micro droplet into a reaction well and a reaction processing method using the same.

The present invention decreases the contact area of a surface to which a liquid droplet is expected to attach as much as possible or facilitates falling of a liquid droplet to thereby urge falling of the liquid droplet itself by gravitation when the amount of a liquid sample is small and the liquid droplet attaches to a wall surface, the ceiling, or the like of the well and does not fall.

A first aspect of a micro droplet operation device of the present invention includes a base plate, a well formed in the base plate and having an opening in one surface of the base plate, a cover plate covering the opening of the well and attached to the one surface of the base plate, a liquid introduction channel constituted from a groove formed in a contact surface between the base plate and the cover plate and connected to the well, an air vent mechanism constituted from a groove formed in the contact surface separately from the liquid introduction channel and connected to the well at a position different from the liquid introduction channel, and a recess disposed in the cover plate and opposite to the well and recessed upward from the upper surface of the liquid introduction channel. In addition, the first aspect is characterized in that at least in the vicinity of a connection part between the well and the liquid introduction channel, when viewed from above, the shoulder part of the recess is disposed closer to the center of the well than the shoulder part of the well or at the same position as the shoulder part of the well.

Here, the vicinity of the connection part between the well and the liquid introduction channel refers to the range in which a liquid possibly comes into contact with the inner wall of a space formed by the well and the recess when the liquid is introduced into the well from the liquid introduction channel.

According to the first aspect, the area with which a liquid droplet that is injected from the liquid introduction channel comes into contact can be made small as compared with the case where the part facing the well of the cover plate is flat, whereby the liquid droplet is facilitated to fall to the bottom of the well by the weight of the droplet itself. This makes it possible to precisely inject a liquid sample.

In a micro droplet operation device of the present invention, the air vent mechanism may be a channel formed by a groove or through hole, or for example, a pore formed by a hydrophobic porous membrane or the like.

The groove constituting the liquid introduction channel can be formed in the cover plate or in the base plate, or in both of them. As the width and depth of the liquid introduction channel in the invention are, for example, about 1 mm (millimeter) each, microfabrication is preferably performed only in either the cover plate or the base plate rather than in both the plates in view of facilitation of the production process. However, the groove may be processed in both of the plates.

Additionally, one example can be mentioned in which the groove constituting the liquid introduction channel is formed in the cover plate and in the vicinity of the connection part between the well and the liquid introduction channel, when viewed from above, the shoulder part of the recess is disposed closer to the center of the well than the shoulder of the well and the liquid introduction channel is formed to extend onto the well and connected to the recess.

Moreover, the groove constituting the liquid introduction channel is formed in the cover plate, when viewed from above, the shoulder part of the recess is disposed closer to the center of the well than the shoulder of the well in the connection part between the well and the liquid introduction channel, and the liquid introduction channel is formed to extend onto the well and has an interval from the recess. The part between the liquid introduction channel and the recess in the cover plate may be formed as a protrusion relative to the groove depth of the liquid introduction channel, not as a recess. In addition, the area of the protrusion is preferably small in order to make the area in which a liquid droplet possibly comes into contact with the cover plate small.

As a micro droplet easily attaches to the plate having a face of a contact angle with the droplet of 90° or smaller, in a construction including the protrusion, the face to which a liquid droplet is expected to attach may be a face of a contact angle with the droplet of 90° or larger. In other words, the protrusion face opposite to the well is preferably subjected to surface treatment such that the contact angle with a liquid droplet is 90° or larger. As a result, a micro droplet repels at the surface of the protrusion subjected to surface treatment. The area with which the micro droplet comes into contact is made small, whereby the droplet is facilitated to fall into the well by its own weight.

The contact angle of a liquid droplet with a face is defined by Young's equation (surface tension of solid $\gamma_S$=surface tension of solid/liquid $\gamma_{SL}$+surface tension of liquid $\gamma_L \cos \theta$). In the present claim and specification, the contact angle means a contact angle in a horizontal plane.

Additionally, in the first aspect of the micro droplet operation device of the present invention, at least a part of the bottom face of the recess, or at least the side of the recess, or both of them can be made so that the contact angle with the liquid droplet is 90° or larger. Thus, even when the micro droplet touches the bottom face or the side of the recess, the micro droplet is facilitated to fall into the well by its own weight.

A second aspect of a micro droplet operation device of the present invention includes a base plate, a well formed in the base plate and having an opening in one surface of the base plate, a cover plate covering the opening of the well and attached to the one surface of the base plate, a liquid introduction channel constituted from a groove formed in a contact surface between the base plate and the cover plate and connected to the well, and an air vent mechanism constituted from a groove formed in the contact surface separately from the liquid introduction channel and connected to the well at a position different from the liquid introduction channel. In addition, the second aspect is characterized in that a part or the whole of the part facing the well in the cover plate is subjected to surface treatment so that the contact angel with a liquid droplet is 90° or larger. The part opposite to the well is subjected to surface treatment so that the contact angle with a liquid droplet is made large, whereby a liquid droplet injected from the liquid introduction channel into the well repels at the part having been subjected to surface treatment, and the area with which a micro droplet comes into contact with the ceiling is made small, whereby the droplet is facilitated to fall into the well by its own weight. This makes it possible to precisely inject a liquid sample.

In particular, it is effective where the groove constituting the liquid introduction channel is formed in the cover plate, the liquid introduction channel is formed to extend onto the well, and within the part opposite to the well in the cover plate, at least the part adjacent to the liquid introduction channel has a liquid droplet contact angle of 90° or larger.

A matter to which a material that makes the contact angle with a liquid droplet larger than that of the cover plate surface is applied can be mentioned as one example of surface treatment that enlarges the contact angle with the liquid droplet. For example, for purified water, materials that make the contact angle with purified water larger by being applied to, for example, glass can include, for example, CYTOP (registered trademark) available from Asahi Glass Co., Ltd.

Additionally, in the first and second aspects, when a liquid droplet is introduced into the well through the liquid introduction channel, a liquid of a contact angle less than 90° to the sidewall or a solid made by solidifying a liquid of a contact angle less than 90° to the sidewall may be accommodated in the well in advance in order that the sidewall of the well is wetted with a liquid of a contact angle less than 90° with the sidewall of the well, which is different from the liquid droplet. When a liquid droplet is injected from the liquid introduction channel into the well, a liquid droplet injected from the liquid introduction channel is facilitated to enter the inside of the well along the wall surface within the well if the sidewall of the well is wetted with a liquid of a contact angle less than 90° to the sidewall.

A third aspect of a micro droplet operation device of the present invention includes a base plate, a well formed in the base plate and having an opening in one surface of the base plate, a cover plate covering the opening of the well and attached to the one surface of the base plate, a liquid introduction channel constituted from a groove formed in a contact surface between the base plate and the cover plate and connected to the well, and an air vent mechanism constituted from a groove formed in the contact surface separately from the liquid introduction channel and connected to the well at a position different from the liquid introduction channel. Additionally, the third aspect is characterized in that when a liquid droplet is introduced into the well through the liquid introduction channel, a liquid of a contact angle less than 90° to the sidewall or a solid made by solidifying a liquid of a contact angle less than 90° to the sidewall is accommodated in the well in advance in order that the sidewall of the well is wetted with a liquid of a contact angle less than 90° with the sidewall of the well, which is different from the liquid droplet. When a liquid droplet is injected from the liquid introduction channel into the well, a liquid droplet injected from the liquid introduction channel is facilitated to enter the inside of the well along the wall surface within the well if the sidewall of the well is wetted with a liquid of a contact angle less than 90° to the above sidewall.

In a micro droplet operation device of the present invention, the sidewall of the well may be subjected to embossing, texturing or machining so as to, for example, increase its surface area compared with a flat surface. As a result, a liquid of a contact angle less than 90° can further surely wet the sidewall, and therefore, a liquid droplet injected from the liquid introduction channel is facilitated to fall to the well bottom along the sidewall of the well.

Moreover, if, for example, a groove having a width of several micrometers to several millimeters is formed in the sidewall of the well, a liquid accommodated in advance and having a contact angle less than 90° with the sidewall moves to the top of the side of the well by capillary action to be able to increase the wet area of the sidewall, whereby a liquid droplet injected from the liquid introduction channel is facilitated to enter the inside of the well along the wall surface within the well.

In addition, in a micro droplet operation device of the present invention, one example of the liquid introduction channel includes a groove formed in the contact surface or a through hole formed in the groove and the plate, and a main channel, a metering channel of a predetermined capacity branched from the main channel, and an injection channel of which one end is connected to the metering channel and the other end is connected to the well, wherein the injection channel is formed thinner than the metering channel and does not pass a liquid in a liquid introduction pressure state when a liquid is introduced into the main channel and the metering channel and a purge pressure state when a liquid within the main channel is purged and passes a liquid under pressures higher than those.

The reaction processing method of the present invention is a reaction processing method using the micro droplet operation device of the present invention in which the liquid introduction channel includes the main channel, the metering channel and the injection channel, wherein the main channel and the metering channel are filled with a liquid at an introduction pressure, a gas is flowed into the main channel and the liquid within the main channel is discharged while the liquid is made to remain within the metering channel, and the pressure within the main channel is made much more positive than the introduction pressure or the inside of the well is made a negative pressure or both of the positive and negative pressures, whereby the liquid within the metering channel is injected into the well via the injection channel.

In the first aspect of the micro droplet operation device of the present invention, in the connection part between the well and the liquid introduction channel, when viewed from above, the shoulder part of the recess is disposed closer to the center than the shoulder part of the well, or at the same position as the shoulder part of the well. Thus, the area of the cover plate with which a liquid droplet injected from the liquid introduction channel comes into contact can be made small as compared with the case where the part facing the well of the cover plate is flat, whereby the liquid droplet is facilitated to fall into the bottom of the well by its own weight.

In the second aspect of the micro droplet operation device of the present invention, a part or the whole of the part opposite to the well in the cover plate is subjected to surface treatment so that the contact angle with a liquid droplet is 90° or larger, whereby a liquid droplet injected into the well from the liquid introduction channel repels at the part having been subjected to surface treatment and thus the liquid droplet is facilitated to fall into the well by the weight of the droplet itself.

In the third aspect of the micro droplet operation device of the present invention, when a liquid droplet is introduced into the well via the liquid introduction channel, a liquid having a contact angle less than 90° with the sidewall or a solid made by solidifying a liquid having a contact angle less than 90° with the sidewall is accommodated within the well in advance in order that the sidewall of the well is wetted with a liquid having a contact angle less than 90° with the sidewall of the well, whereby a liquid sample is facilitated to enter the bottom of the well along the sidewall within the well.

Additionally, in the micro droplet operation device of the present invention, the well is made not to touch the external atmosphere, whereby the contamination of a liquid sample from the outside or the outside environmental pollution caused by a liquid sample can be prevented. Moreover, falling of a liquid droplet into the well by the liquid droplet itself can be urged as described above. As a result, the prevention of external environmental pollution, efficiency of analysis and miniaturization of the device are easily achieved.

BRIEF DESCRIPTION OF THE DRAWINGS

FIGS. 9(B1) to 9(B4) are schematic views illustrating the photographs of FIGS. 9(A1) to 9(A4), respectively.

DESCRIPTION OF THE REFERENCE NUMERALS

Figure 1A:
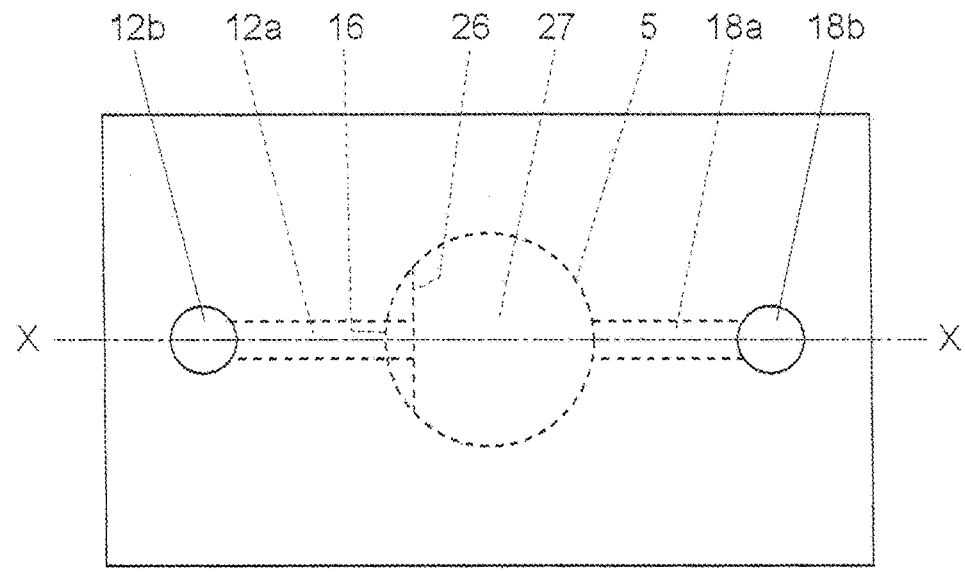
FIG. 1A is a schematic plan view of the liquid droplet operation device in one example of a first aspect.

3: Well base
5: Reaction well
9: Wax
11: Flow passage base
12a: Liquid introduction channel
18a: Air vent channel
12b, 18b: Through hole
27: Recess

DETAIL DESCRIPTION OF THE INVENTION

Examples of the present invention will be described as follows:

Example 1

Figure 1B:
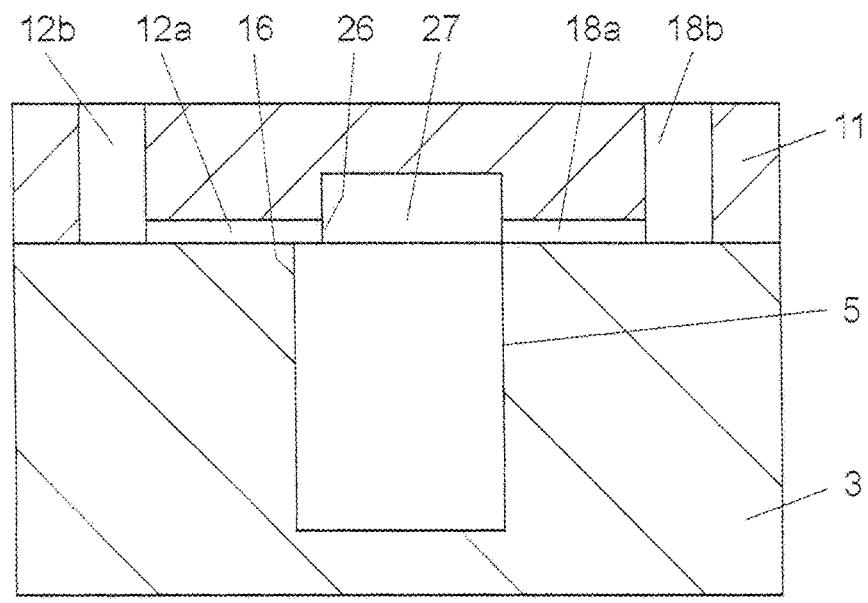
FIG. 1B is a schematic sectional view of the liquid droplet operation device in the example.

FIGS. 1A and 1B are schematic views of the liquid droplet operation device in one example of the first aspect, and FIG. 1A is a plan view and FIG. 1B is a sectional view.

A well base (base plate) 3 includes a cylindrical reaction well (well) 5 having an opening of, for example, an inner diameter of 3 mm and a depth of 10 mm formed in its one surface. The inner diameter and the depth of the reaction well 5 are not particularly limited. A reagent (not shown) is accommodated within the reaction well 5 in advance.

The material of the well base 3 including the reaction well 5 is not particularly limited; however, a material available at low cost is preferred when it is used for a disposable micro droplet operation device. Preferable examples of the material include resin materials such as polypropylene and polycarbonate. When a substance within the reaction well 5 is detected by absorbance, fluorescence, chemoluminescence, bioluminescence, or the like, the well base 3 is preferably made from a light transmissive resin in order to optically detect the substance from the bottom face. In particular, when fluorescence detection is performed, a light transmissive resin with low self-fluorescence properties (property of generating little fluorescence from the resin itself) such as polycarbonate is preferred as a material of the well base 3. The thickness of the well base 3 is from 0.2 to 4.0 mm. The thickness of the well base 3 is preferably small from the viewpoint of low self-fluorescence properties for fluorescence detection.

A channel base (cover plate) 11 covering the reaction well 5 is disposed on the well base 3. The channel base 11 is made of, for example, polydimethylsiloxane (PDMS), silicone rubber, or the like. The thickness of the channel base 11 is, for example, between 1.0 and 5.0 mm.

The channel base 11 has a groove in the contact surface with the well base 3. A liquid introduction channel 12a and a reaction well air vent channel (air vent mechanism) 18a are formed by the groove and the surface of the well base 3. The width and depth of the liquid introduction channel 12a are, for example, 1,000 μm or less. A liquid containing DNA required to be amplified by PCR is flowed in the liquid introduction channel 12a. Moreover, the width and the depth of the reaction well air vent channel 18a are, for example, 1,000 μm or less. The reaction well air vent channel 18a is used as a channel for air vent from the reaction well 5.

One end of the liquid introduction channel 12a is connected to a through hole 12b utilized for the introduction of a liquid, one the other end is connected to the reaction well 5. In addition, one end of the reaction well air vent channel 18a is connected to a through hole 18b utilized for the discharge of air, and the other end is connected to the reaction well 5 at a position other than the position at which the other end of the liquid introduction channel 12a is connected to the reaction well. A syringe pump and the like are connected to the through hole 12b to introduce a liquid sample, and a drain is connected to the through hole 18b to discharge air. In this example, although the through hole 12b and the through hole 18b are formed in the channel base 11, they may be formed in the well base 3. Additionally, the liquid introduction channel 12a and the reaction well air vent channel 18a may be formed in the channel base 11, or in both of the bases 3 and 11.

A recess 27 is formed in the surface of the channel base 11 which is opposite to the reaction well 5. The recess 27 is formed deeper than the groove depth of the liquid introduction channel 12a and disposed to be dented upward of the upper surface of the liquid introduction channel 12a. In the vicinity of the connection part between the reaction well 5 and the liquid introduction channel 12a, when viewed from above (see FIG. 1A), a shoulder part 26 of the recess 27 is placed closer to the center of the reaction well 5 than a shoulder part 16 of the reaction well 5.

Next, the operation of the example will be set forth.

The method of use includes, for example, sampling 3 μL of a liquid sample using a syringe pump, feeding the sample at 200 μL/min (microliter/min) (arbitrary speed) from the through hole 12b, and feeding the sample into the reaction well 5 through the liquid introduction channel 12a. Along with this feeding, some gas within the reaction well 5 is discharged to a drain from the through hole 18b via the reaction well air vent channel 18a.

In the liquid droplet operation device of Example 1, the depth of the recess 27 disposed facing the reaction well 5 is deeper than the depth of the liquid introduction channel 12a so that the area of a liquid sample with which the part of the channel base 11 (part opposite to the opening of the reaction well 5) comes into contact is made small. In addition, the shoulder part 26 of the recess 27 is placed closer to the center of the reaction well 5 than the shoulder part 16 of the reaction well 5 is. As a result, the area of a liquid sample with which the channel base 11 comes into contact is reduced and the weight of the liquid sample itself becomes larger than the force of the interaction of the liquid sample with the channel base 11, whereby the liquid sample is facilitated to fall into the bottom of the reaction well 5 in which, for example, a reagent required for PCR reaction is accommodated.

Figure 24:
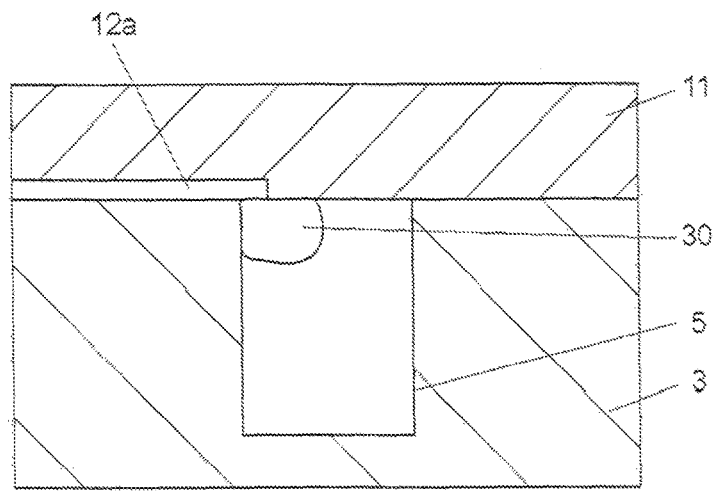
FIG. 24 is a schematic plan view of a conventional liquid droplet operation device.

In a conventional micro droplet operation device (see FIG. 24), for example, in the case where purified water as a liquid sample and glass as a material of the channel base 11 are used, when purified water comes into contact with the channel base 11, hydrogen atoms constituting the purified water and oxygen atoms constituting the glass are attracted to each other due to their interaction, and as a result, the liquid droplet remains on the ceiling face due to the interaction. In the present invention, the area of a liquid sample with which the channel base 11 comes into contact is reduced within the reaction well 5 in order to decrease the interaction between the liquid sample and the channel base 11 within the reaction well 5, and therefore, a droplet of the liquid sample can be refrained from remaining on the ceiling face of the reaction well 5.

Example 2

Figure 2A:
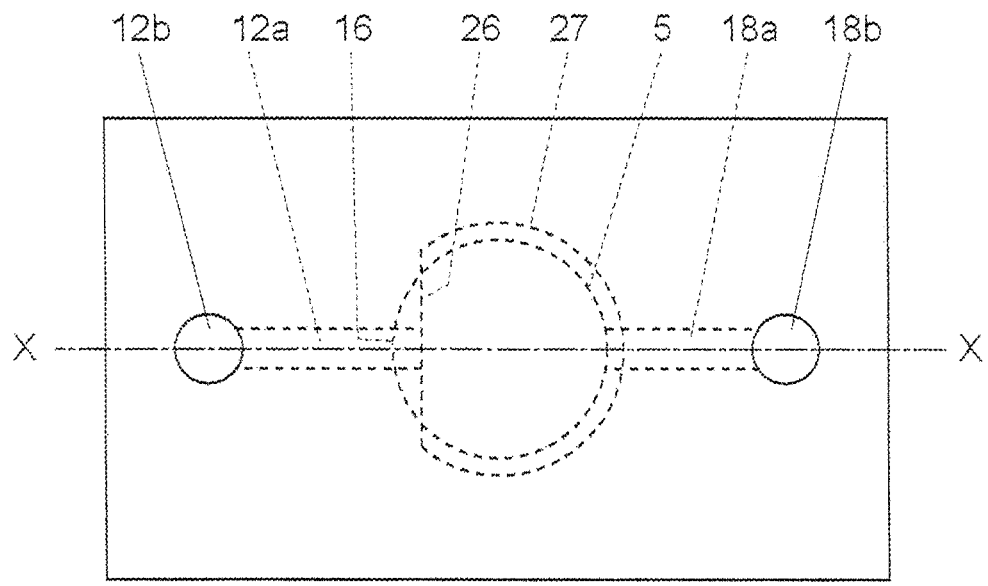
FIG. 2A is a schematic plan view of the liquid droplet operation device in another example of the first aspect.
Figure 2B:
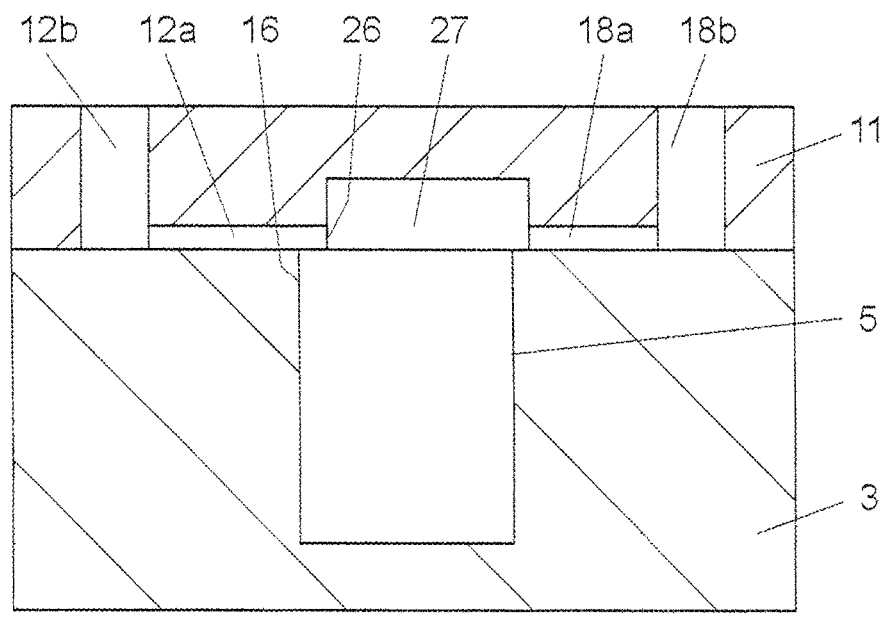
FIG. 2B is a schematic sectional view of the liquid droplet operation device in the example.

FIGS. 2A and 2B are schematic views of the liquid droplet operation device in another example of the first aspect. FIG. 2A is a plan view and FIG. 2B is a sectional view.

The difference of this example from Example 1 is that, when viewed from above (see FIG. 2A), the shoulder part 26 of the recess 27 is disposed more outside the reaction well 5 than the shoulder part 16 of the reaction well 5 except in the vicinity of the connection part between the reaction well 5 and the liquid introduction channel 12a. In the vicinity of the connection part between the reaction well 5 and the liquid introduction channel 12a, as in Example 1, the shoulder part 26 of the recess 27 is disposed closer to the center of the reaction well 5 than the shoulder part 16 of the reaction well 5.

Thus, when a liquid sample is introduced from the liquid introduction channel 12a into the reaction well 5, if the shoulder part 26 of the recess 27 is disposed closer to the center of the reaction well 5 than the shoulder part 16 of reaction well 5 is, in the range in which the liquid possibly comes into contact with the inner wall of the space formed by the reaction well 5 and the recess 27, or in the vicinity of the connection part between the reaction well 5 and the liquid introduction channel 12a, the liquid sample is facilitated to fall into the bottom of the reaction well 5 from the liquid introduction channel 12a.

Example 3

Figure 3A:
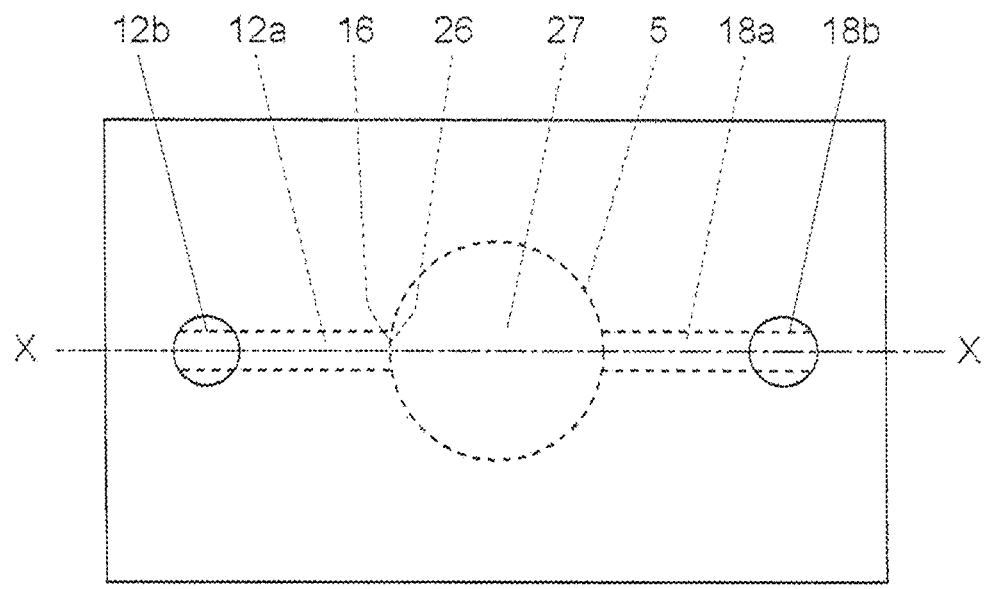
FIG. 3A is a schematic plan view of the liquid droplet operation device in still another example of the first aspect.
Figure 3B:
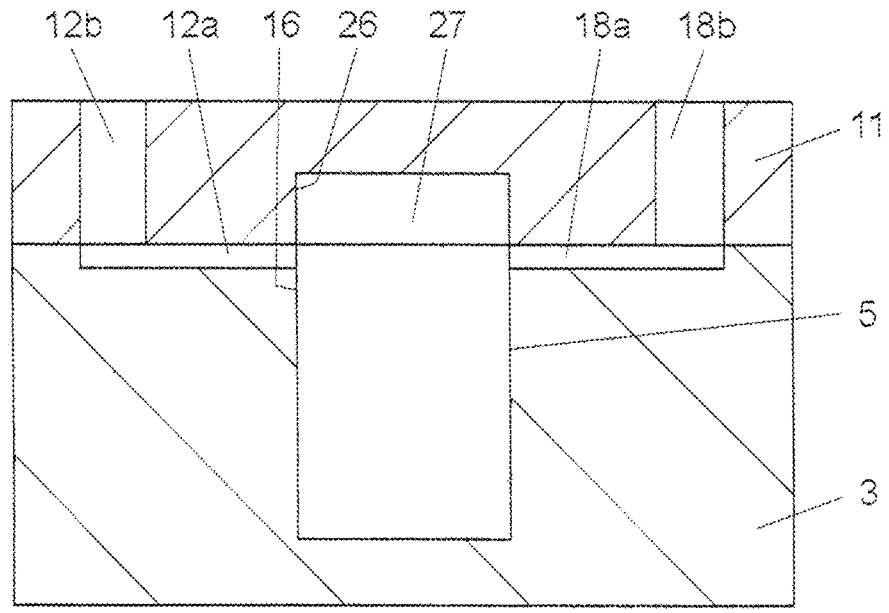
FIG. 3B is a schematic sectional view of the liquid droplet operation device in the example.

FIGS. 3A and 3B are schematic views of the liquid droplet operation device in still another example of the first aspect, and FIG. 3A is a plan view and FIG. 3B is a sectional view.

As in Example 1, the cylindrical reaction well 5 is formed in one surface of the well base 3 and a reagent (not shown) is contained in the reaction well 5 in advance. The channel base 11 covering the reaction well 5 is disposed on the well base 3.

The well base 3 includes a groove in the contact surface with the channel base 11. The liquid introduction channel 12a and the reaction well air vent channel 18a are formed by the groove and the surface of the well base 11. The width and the depth of the liquid introduction channel 12a are 1,000 μm or less, and for example, a liquid containing DNA required to be amplified by PCR is flowed. Moreover, the width and the depth of the reaction well air vent channel 18a are 1,000 μm or less and the passage is used as a channel for air vent from the reaction well 5.

As in Example 1, one end of the liquid introduction channel 12a is connected to the through hole 12b utilized for the introduction of a liquid, and the other end is connected to the reaction well 5. In addition, one end of the reaction well air vent channel 18a is connected to the through hole 18b utilized for the discharge of air, and the other end is connected to the reaction well 5 at a position other than the position at which the other end of the liquid introduction channel 12a is connected to the reaction well.

The recess 27 is formed in the surface of the channel base 11 which is opposite to the reaction well 5. The recess 27 is formed deeper than the groove depth of the liquid introduction channel 12a. In addition, in the connection part of the reaction well 5 and the liquid introduction channel 12a, when viewed from above (see FIG. 3A), the shoulder part 26 of the recess 27 is placed at the same position as the shoulder part 16 of the reaction well 5.

In this Example 2, a liquid droplet of a liquid sample does not come into contact with the bottom face of the recess 27 opposite to the reaction well 5 of the channel base 11, and the weight of the liquid sample itself is larger than the force of the interaction between a liquid droplet of the liquid sample and the wall surface of the recess 27, and therefore, the liquid sample is facilitated to fall into the bottom of the reaction well. Additionally, the channels 12a and 18a may be formed in the well base 11, or in both of the bases 3 and 11.

Example 4

Figure 4A:
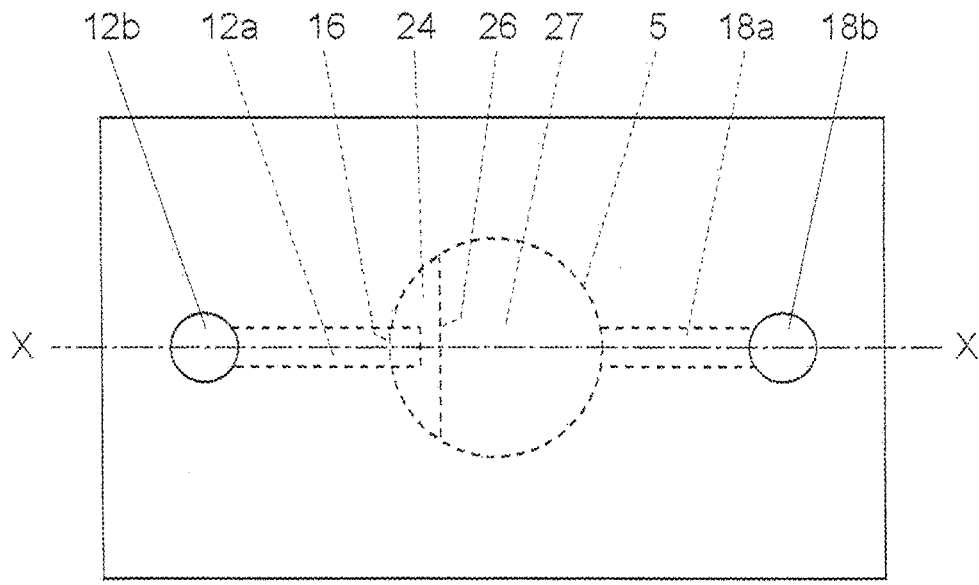
FIG. 4A is a schematic plan view of the liquid droplet operation device in still another example of the first aspect.
Figure 4B:
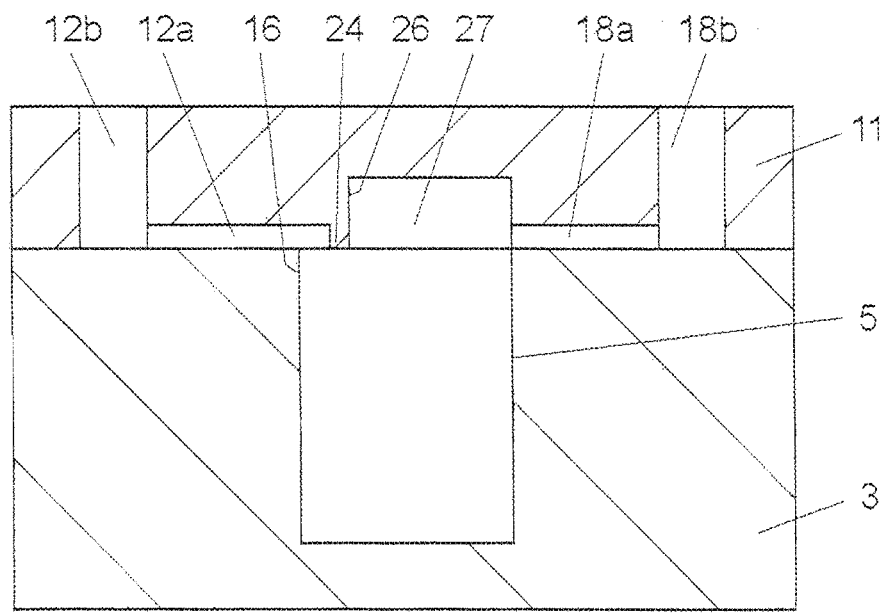
FIG. 4B is a schematic sectional view of the liquid droplet operation device in the example.

FIGS. 4A and 4B are schematic views of the liquid droplet operation device in still another example of the first aspect. FIG. 4A is a plan view and FIG. 4B is a sectional view.

As in Example 1, the cylindrical reaction well 5 is formed in one surface of the well base 3 and a reagent (not shown) is contained in the reaction well 5 in advance. The channel base 11 covering the reaction well 5 is disposed on the well base 3. The channel base 11 includes a groove in the contact surface with the well base 3, and the liquid introduction channel 12*a* and the reaction well air vent channel 18*a* are formed by the groove and the surface of the well base 3.

One end of the liquid introduction channel 12*a* is connected to the through hole 12*b* utilized for the introduction of a liquid, and the other end is connected to the reaction well 5. In addition, one end of the reaction well air vent channel 18*a* is connected to the through hole 18*b* utilized for the discharge of air, and the other end is connected to the reaction well 5 at a position other than the position at which the other end of the liquid introduction channel 12*a* is connected to the reaction well.

The recess 27 is formed deeper than the groove depth of the liquid introduction channel 12*a* in the surface of the channel base 11 which is opposite to the reaction well 5. Additionally, in the connection part between the reaction well 5 and the liquid introduction channel 12*a*, when viewed from above (see FIG. 4A), the shoulder part 26 of the recess 27 is placed closer to the center of the reaction well 5 than the shoulder part 16 of the reaction well 5. The part between the liquid introduction channel 12*a* and the recess 27 is not formed as a recess but is a protrusion 24 relative to the groove depth of the liquid introduction channel 12*a*.

In one example, the groove depth of the liquid introduction channel 12*a* is 400 µm, the depth of the recess 27 is 1.5 mm, and the height of the protrusion 24 is 400 µm relative to the groove depth.

In Example 3, a recess serving as a groove is not disposed between the liquid introduction channel 12*a* and the recess 27, and inversely the protrusion 24 convex-shaped relative to the depth of the liquid introduction channel 12*a* is formed.

The protrusion 24 has a small area where a liquid droplet can come into contact as compared with the channel base 11 disposed opposite to the reaction well 5, so the micro droplet hardly comes into contact with the channel base 11 and, thus, is facilitated to fall into the bottom of the reaction well 5 by its own weight. In addition, the area of the protrusion 24 is preferably small in order to make the area in which a liquid droplet possibly comes into contact with the base plate 11 small.

Example 5

Figure 5A:
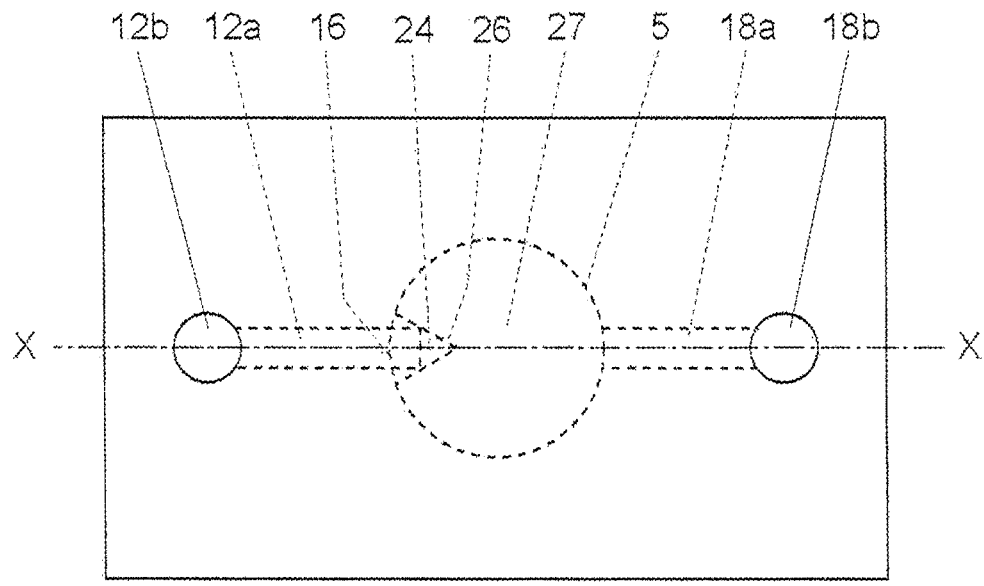
FIG. 5A is a schematic plan view of the liquid droplet operation device in still another example of the first aspect.
Figure 5B:
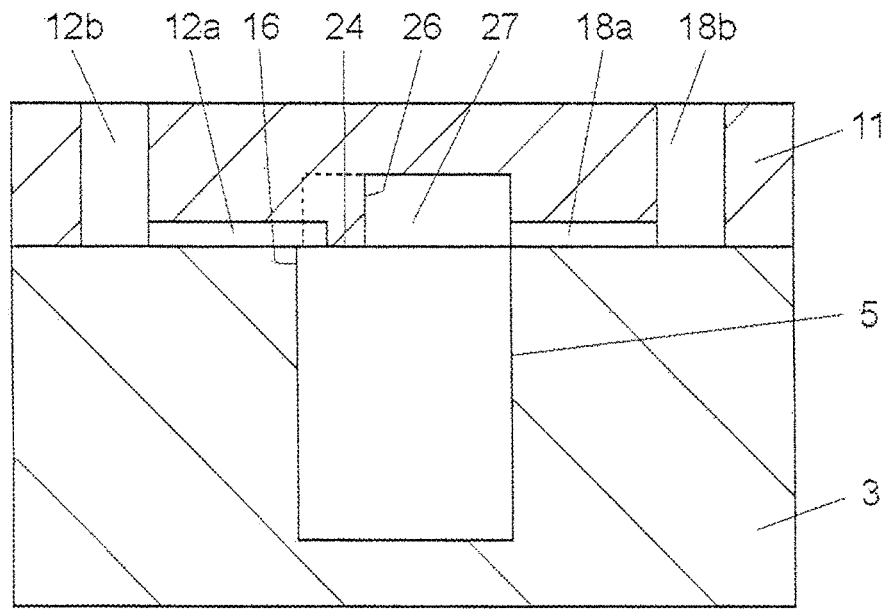
FIG. 5B is a schematic sectional view of the liquid droplet operation device in the example.

FIGS. 5A and 5B are schematic views of the liquid droplet operation device in still another example of the first aspect. FIG. 5A is a plan view and FIG. 5B is a sectional view.

As in Example 1, the cylindrical reaction well 5 is formed in one surface of the well base 3 and a reagent (not shown) is contained in the reaction well 5 in advance. The channel base 11 covering the reaction well 5 is disposed on the well base 3. The channel base 11 includes a groove in the contact surface with the well base 3, and the liquid introduction channel 12*a* and the reaction well air vent channel 18*a* are formed by the groove and the surface of the well base 3.

One end of the liquid introduction channel 12*a* is connected to the through hole 12*b* utilized for the introduction of a liquid, one the other end is connected to the reaction well 5. In addition, one end of the reaction well air vent channel 18*a* is connected to the through hole 18*b* utilized for the discharge of air, and the other end is connected to the reaction well 5 at a position other than the position at which the other end of the liquid introduction channel 12*a* is connected to the reaction well.

The recess 27 is formed deeper than the groove depth of the liquid introduction channel 12*a* in the surface of the channel base 11 which is opposite to the reaction well 5. Additionally, in the connection part between the reaction well 5 and the liquid introduction channel 12*a*, when viewed from above (see FIG. 5A), the shoulder part 26 of the recess 27 is placed closer to the center of the reaction well 5 than the shoulder part 16 of the reaction well 5 is. The part between the liquid introduction channel 12*a* and the recess 27 is not formed as a recess but is a protrusion 24 relative to the groove depth of the liquid introduction channel 12*a*.

Although the protrusion 24 between the liquid introduction channel 12*a* and the reaction well 5 in Example 3 is expanded in the planar direction perpendicular to the liquid introduction channel 12*a*, in Example 4, the protrusion 24 is formed to surround the tip of the channel 12*a* in plan view so that the area of the protrusion 24 becomes as small as possible.

As a result, a sample injected from the liquid introduction channel 12*a* comes into contact with the protrusion 24 prior to reaching the recess 27 and is thus prevented from sticking to the recess 27, and therefore, the droplet is facilitated to fall into the reaction well 5 by weight. In addition, since the contact area of the liquid droplet with the protrusion 24 becomes small as compared with the case of Example 3 described using FIGS. 4A and 4B, the liquid droplet hardly interacts with the protrusion 24, making it difficult for the liquid droplet to remain in the channel base 11 and is facilitated to fall into the reaction well 5.

Example 6

Figure 6A:
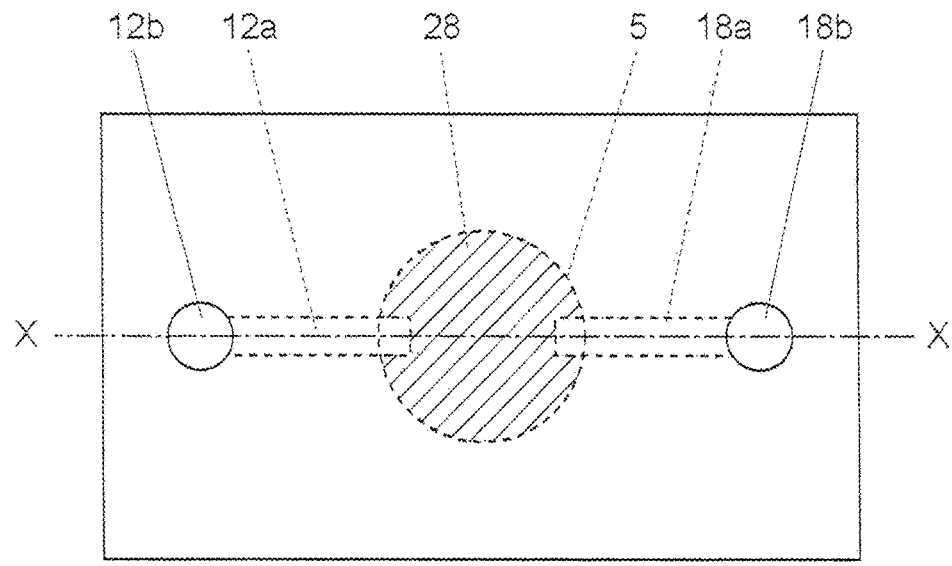
FIG. 6A is a schematic plan view of the liquid droplet operation device in one example of a second aspect.
Figure 6B:
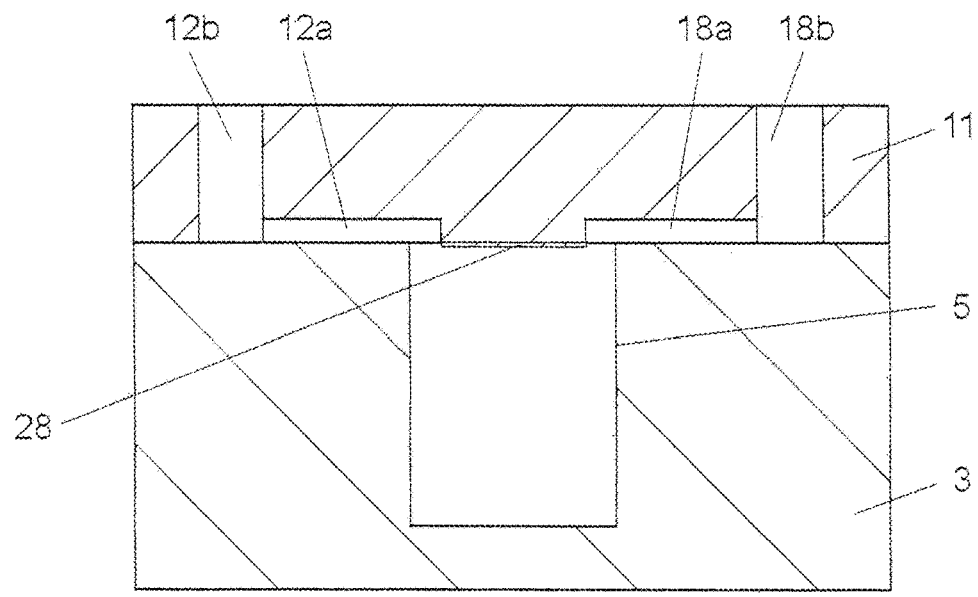
FIG. 6B is a schematic sectional view of the liquid droplet operation device in the example.

FIGS. 6A and 6B are schematic views of the liquid droplet operation device in an example of the second aspect, and FIG. 6A is a plan view and FIG. 6B is a sectional view.

As in Example 1, the cylindrical reaction well 5 is formed in one surface of the well base 3 and a reagent (not shown) is contained in the reaction well 5 in advance. The channel base 11 covering the reaction well 5 is disposed on the well base 3. The channel base 11 includes a groove in the contact surface with the well base 3, and the liquid introduction channel 12*a* and the reaction well air vent channel 18*a* are formed by the groove and the surface of the well base 3.

One end of the liquid introduction channel 12*a* is connected to the through hole 12*b* utilized for the introduction of a liquid, and the other end is connected to the reaction well 5. In addition, one end of the reaction well air vent channel 18*a* is connected to the through hole 18*b* utilized for the discharge of air, and the other end is connected to the reaction well 5 at a position other than the position at which the other end of the liquid introduction channel 12*a* is connected to the reaction well.

A membrane 28 is formed on the face in the channel base 11 which is opposite to the reaction well 5. In this example, the membrane 28 is formed on the whole part of the channel base 11 which is opposite to the reaction well 5, excluding the formation positions of the channels 12*a* and 16*a*. The membrane 28 is formed by subjecting the surface to surface treatment so that the contact angle becomes larger than the contact angle relative to the channel base 11. The contact angle of a liquid droplet with the membrane 28 is 90° or larger. The surface treatment in order to make the contact angle of a liquid droplet with the membrane 28 larger than the contact angle of the liquid droplet with the channel base 11 can be achieved by applying CYTOP (registered trademark) available from Asahi Glass Co., Ltd. when purified water is a sample, for example.

According to this example, a liquid droplet injected from the liquid introduction channel 12*a* into the reaction well 5 repels at the membrane 28 subjected to surface treatment and is facilitated to fall into the reaction well 5 by its own weight.

Although the position for forming the membrane 28 may be the whole part of the face of the channel base 11 which is opposite to the reaction well 5, or a part of the face, the contact angle with a liquid droplet is preferably 90° or larger in the part adjacent to the liquid introduction channel 12*a*.

This surface treatment can also be applied to the bottom face, the side face, or both of them, of the recess 27 in Examples 1 to 5. As a result, a liquid droplet introduced from the liquid introduction channel 12*a* hardly sticks to the inner wall surface of the recess 27 of the channel base 11 and thus is facilitated to fall into the reaction well 5.

Example 7

When a liquid sample is injected from the liquid introduction channel 12*a*, the liquid droplet attaches to the sidewall of the reaction well 5 in the case where the amount of a sample is small, and therefore, the liquid droplet sometimes does not fall into the well by its own weight. Hence, a liquid droplet attached to the sidewall of the reaction well 5 is preferably facilitated to fall into the reaction well 5.

Figure 7A:
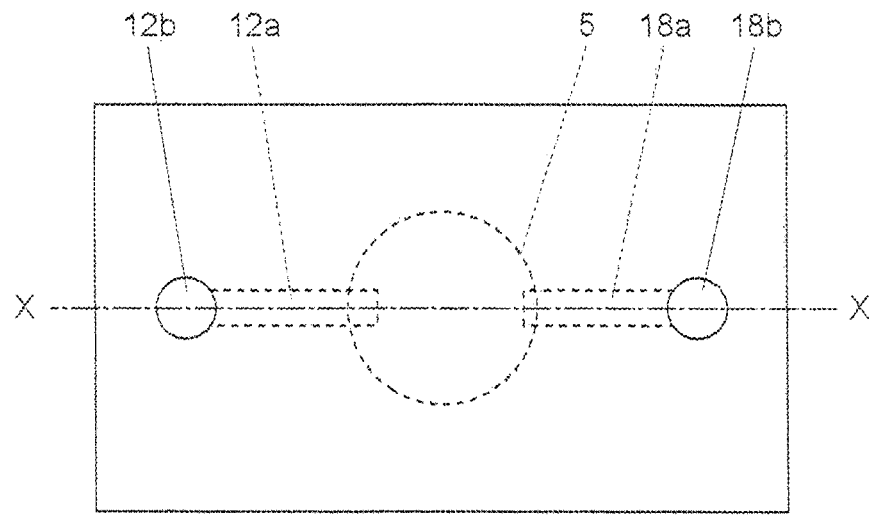
FIG. 7A is a schematic plan view of the liquid droplet operation device in one example of a third aspect.
Figure 7B:
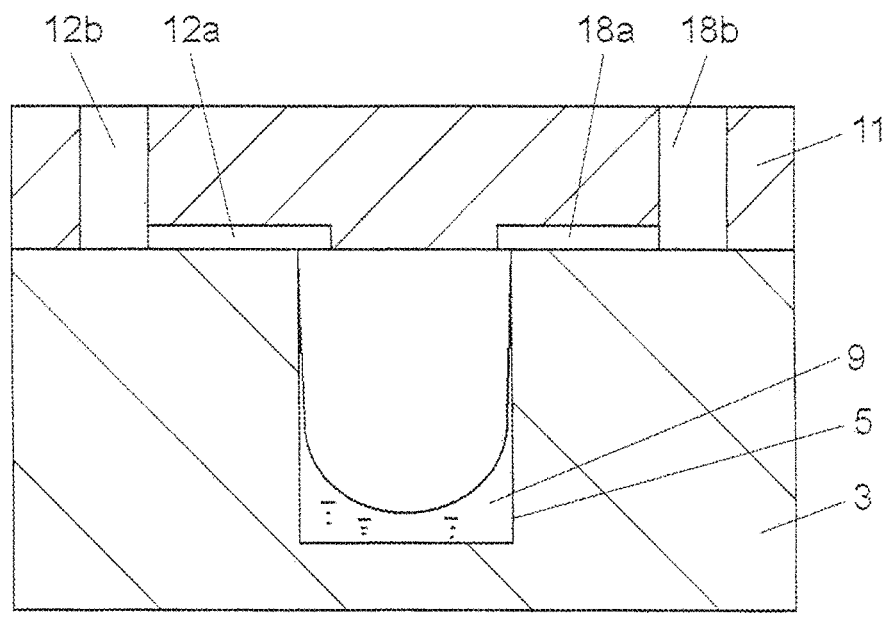
FIG. 7B is a schematic sectional view of the liquid droplet operation device in the example.
Figure 7C:
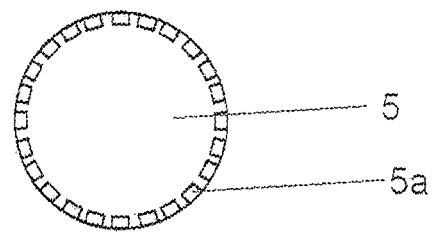
FIG. 7C is a schematic sectional view of a reaction well of the liquid droplet operation device in the example.
Figure 7D:
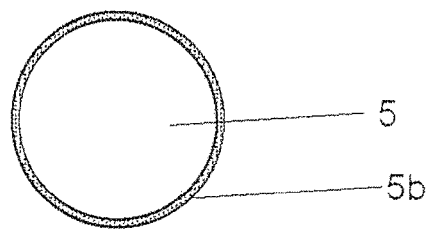
FIG. 7D is a schematic sectional view of the reaction well of the liquid droplet operation device in the example.

FIGS. 7A to 7D are schematic views of the liquid droplet operation device in an example of the third aspect for realizing the above object, and FIG. 7A is a plan view and FIG. 7B is a sectional view. FIGS. 7C and 7D show one example of a sectional view of the reaction well 5.

As in Example 1, the reaction well 5 is formed in one surface of the well base 3. A reagent (not shown) is accommodated within the reaction well 5 in advance. The channel base 11 covering the reaction well 5 is disposed on the well base 3. The channel base 11 includes a groove in the contact surface with the well base 3, and the liquid introduction channel 12*a* and the reaction well air vent channel 18*a* are formed by the groove and the surface of the well base 3.

One end of the liquid introduction channel 12*a* is connected to the through hole 12*b* utilized for the introduction of a liquid, and the other end is connected to the reaction well 5. In addition, one end of the reaction well air vent channel 18*a* is connected to the through hole 18*b* utilized for the discharge of air, and the other end is connected to the reaction well 5 at a position other than the position at which the other end of the liquid introduction channel 12*a* is connected to the reaction well.

Wax 9 with a small contact angle with the sidewall, which is different from a liquid droplet injected from the liquid introduction channel 12*a* and subjected to manipulation, is introduced into the reaction well 5 in advance, and the sidewall of the reaction well 5 is wet due to this wax 9, whereby the frictional resistance on the sidewall becomes small. In addition, a reagent (not shown) contained in the reaction well 5 is larger in specific gravitation than the wax 9 and remains on the bottom of the reaction well 5.

In this example, wax that is cured at room temperature is mixed with a mineral oil that is readily handled as a liquid having a small contact angle with the sidewall and the mixed liquid of the mineral oil and the wax is contained in the reaction well in advance. In addition, a liquid droplet operation device including the channel base 11 and the well base 3 is heated to 90° C. to dissolve the mixed liquid of the mineral oil and the wax, and the resulting liquid rises along the sidewall of the polypropylene reaction well 5 to wet the sidewall of the upper part of the reaction well 5. In this state, a liquid sample is injected into the reaction well 5 from the liquid introduction channel 12*a*, whereby the liquid sample slides down the sidewall of the reaction well 5 to fall to the lower part of the reaction well 5.

Additionally, the sidewall of the reaction well 5 may be provided with a groove or the like, or roughened to thereby increase the surface area of the sidewall. This processing can be carried out by a method such as embossing by sand blasting, texturing, or machining.

FIG. 7C is a diagram in which embossing is applied to the sidewall of the reaction well 5. A plurality of grooves 5*a* are formed in the depth direction of the reaction well 5. The widths and the intervals of the grooves 5*a* are, for example, hundreds of micrometers to several millimeters. The wax 9 within the reaction well 5 rises along the sidewall of the well by capillary action, and the sidewall of the reaction well 5 is prone to wet with the wax 9.

FIG. 7D is a diagram in which texturing is applied to the sidewall of the reaction well 5. The mean interval of convexoconcaves 5*b* by texturing is, for example, several micrometers to several hundreds of micrometers. As the surface area of the sidewall of the reaction well 5 is increased by this fine texturing, in the case where the contact angle with the sidewall of the reaction well 5 is small as compared to the case of a flat surface, the contact angle becomes smaller, whereby the sidewall of the reaction well 5 is facilitated to wet with the wax 9.

The surface area of the side of the reaction well 5 is increased as described above as compared with the case of a flat surface, whereby the wax 9 spread to the entire side of the reaction well 5, and when a liquid droplet is injected into the reaction well 5, the liquid droplet is prone to fall into the reaction well 5 along the sidewall of the reaction well 5 that is wet with the wax 9.

The surface treatment facilitating to wet the sidewall of this reaction well 5 may be applied to the reaction well 5 in Examples 1 to 5, in which the wax 9 is not accommodated within the reaction well 5. In that case, the liquid droplet hardly sticks to the channel base 11 and is facilitated to fall into the reaction well 5.

Example 8

Figure 8A:
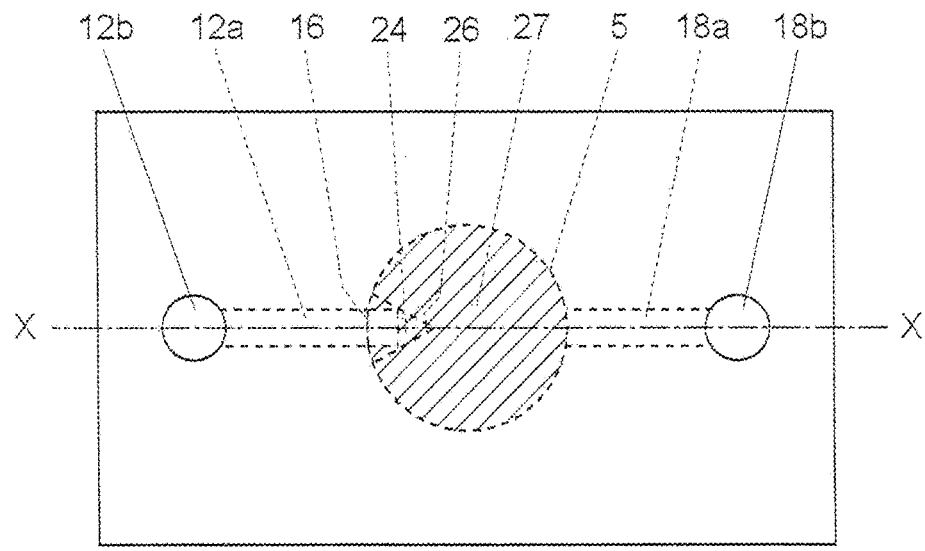
FIG. 8A is a schematic plan view of the liquid droplet operation device in an example of the first, second and third aspects.
Figure 8B:
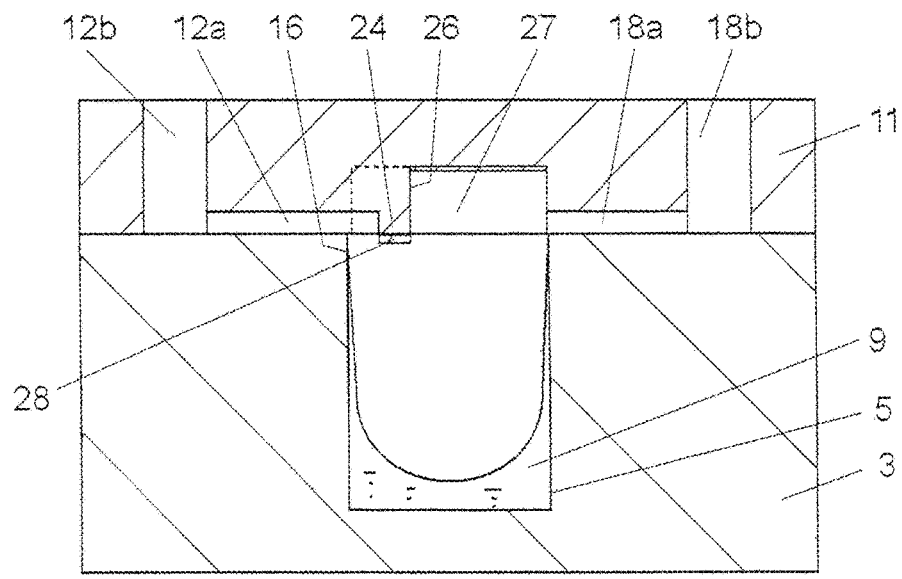
FIG. 8B is a schematic sectional view of the liquid droplet operation device in the example.

FIGS. 8A and 8B are schematic views of the liquid droplet operation device in an example of a combination of the first, second, and third aspects, and FIG. 8A is a plan view and FIG. 8B is a sectional view.

In Examples 1 to 3, the face opposite to the reaction well 5 of the channel base 11 was made to have a recess shape. The protrusion 24 was provided between the liquid introduction channel 12*a* and the recess 27 in Examples 4 and 5. In Example 6, processing was performed that enlarges the contact angle of a liquid droplet injected into the reaction well 5 relative to the face opposite to the reaction well 5 of the channel base 11. In Example 7, surface treatment was carried out on the sidewall of the reaction well 5 that makes the contact angle of a liquid accommodated in advance within the reaction well 5 small relative to the sidewall. Example 8 is an example that combines these.

As in Example 7, the reaction well 5 is formed in one surface of the well base 3 and a reagent (not shown) is contained in the reaction well 5 in advance. The channel base 11 covering the reaction well 5 is disposed on the well base 3. The channel base 11 includes a groove in the contact surface with the well base 3, and the liquid introduction channel 12a and the reaction well air vent channel 18a are formed by the groove and the surface of the well base 3.

One end of the liquid introduction channel 12a is connected to the through hole 12b utilized for the introduction of a liquid, and the other end is connected to the reaction well 5. In addition, one end of the reaction well air vent channel 18a is connected to the through hole 18b utilized for the discharge of air, and the other end is connected to the reaction well 5 at a position other than the position at which the other end of the liquid introduction channel 12a is connected to the reaction well.

The recess 27 is formed deeper than the groove depth of the liquid introduction channel 12a in the surface of the channel base 11 which is opposite to the reaction well 5. In the connection part between the reaction well 5 and the liquid introduction channel 12a, when viewed from above (see FIG. 8A), the shoulder part 26 of the recess 27 is placed closer to the center of the reaction well 5 than the shoulder part 16 of the reaction well 5 is. The part between the liquid introduction channel 12a and the recess 27 is not formed as a recess, but is the protrusion 24 relative to the groove depth of the liquid introduction channel 12a and is formed so as to surround the tip of the channel 12a so that the area of the protrusion 24 becomes small.

The recess 27 opposite to the opening of the reaction well 5 in the channel base 11 is subjected to surface treatment that makes the contact angle larger than that to the channel base 11. In addition, the wax 9 prone to wet, which is different from the manipulating droplet, is introduced within the reaction well 5, and the introduction of this wax 9 makes the frictional resistance of the sidewall of the reaction well 5 small.

When a liquid sample comes into contact with the well wall and falls along the sidewall, the gravitation added to its own weight of the liquid sample is present in the fall direction and a frictional resistance to the sidewall is present in the direction inverse to the fall direction. When the liquid sample is in a minute amount (e.g., 10 μL or less), the liquid droplet cannot fall because the gravitation of the liquid droplet is smaller than the frictional resistance to the wall. However, when the liquid sample is, for example, purified water, the well sidewall is wetted with, for example, oil as a different liquid to thereby make the frictional resistance small, whereby the liquid sample that has come into contact with the well sidewall can fall by its own weight.

Next, such a phenomenon will be explained using experimental results.

Figure 9:
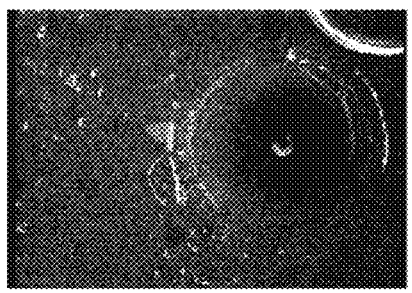
FIGS. 9(A1) to 9(A4) are optical photomicrographs when wax oil is introduced into the reaction well and a liquid droplet is injected thereinto from an injection channel, and show pictures after 0, 1, 2 and 3 seconds in the order of FIG. 9(A1) to FIG. 9(A4).
Figure 9:
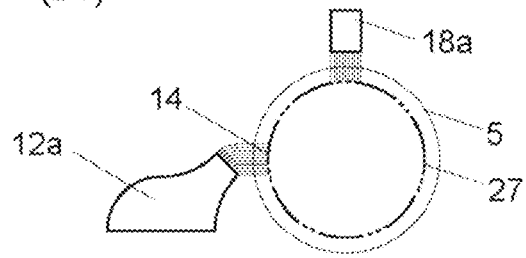
Figure 9:
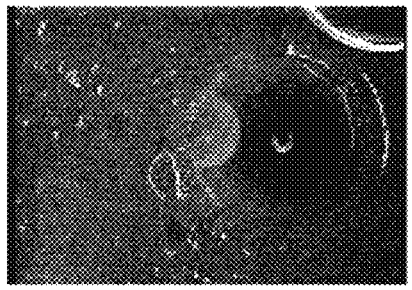
Figure 9:
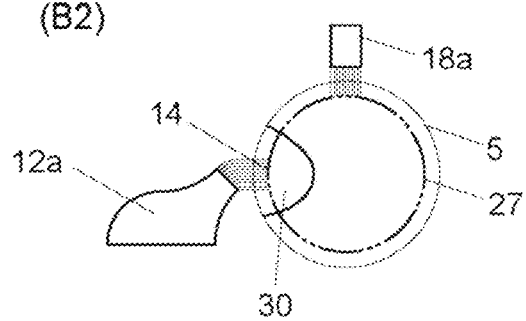
Figure 9:
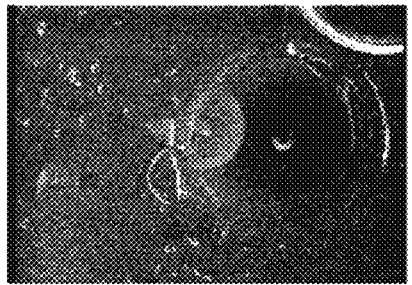
Figure 9:
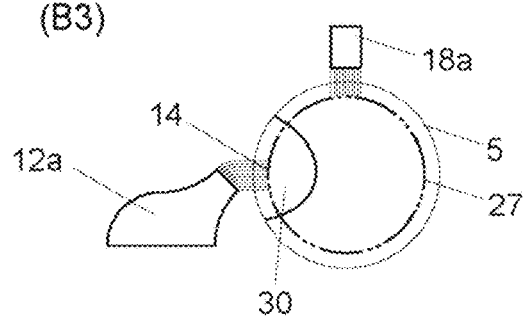
Figure 9:
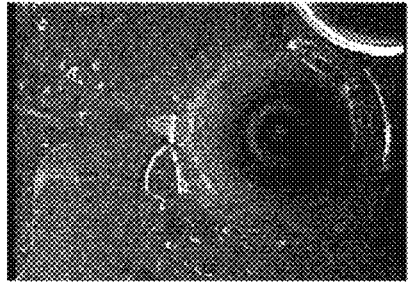
Figure 9:
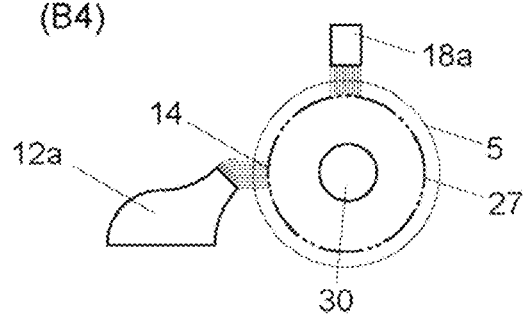

FIGS. 9(A1) to 9(A4) are optical photomicrographs when wax oil is introduced into the reaction well 5 and a liquid droplet is injected thereinto from the liquid injection channel 12a, and show pictures after 0, 1, 2 and 3 seconds in the order of FIG. 9(A1) to FIG. 9(A4). Additionally, FIGS. 9(B1) to 9(B4) are schematic views illustrating the photographs of FIGS. 9(A1) to 9(A4), respectively.

The reaction well 5 is a cylinder and the recess 27 is a cylinder having a diameter smaller than that of the well. The tip of the liquid introduction channel 12a is a passive valve 14, and a liquid droplet is injected into the reaction well 5 therefrom. Moreover, the air vent channel 18a is connected to the reaction well 5.

As shown in FIGS. 9(A1) to 9(A4) and 9(B1) to 9(B4), when a liquid droplet of the liquid sample 30 is introduced from the liquid introduction channel 12a through the passive valve 14, it can be ascertained that the droplet instantaneously (about 1 to 2 sec.) falls into the reaction well 5.

As a result, it is understood that the injected liquid droplet of the liquid sample 30 falls without sticking to the channel base 11 or its recess 27 disposed opposite to the reaction well 5.

Next, the micro droplet operation device and the reaction well processing method using the same of the present invention will be described.

Example 9

Figure 10A:
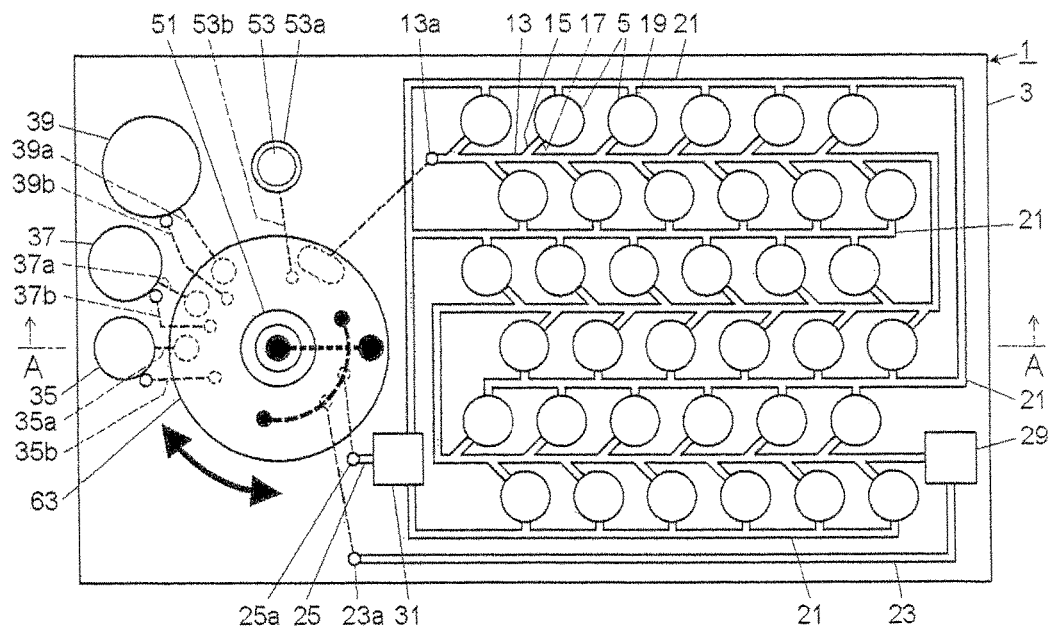
FIG. 10A is a schematic plan view showing one example of a micro droplet operation device.
Figure 10B:
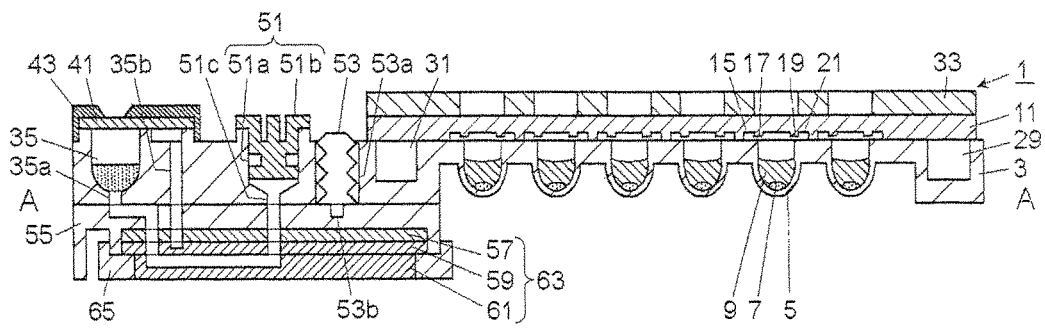
FIG. 10B is a diagram showing the example and is a schematic sectional view in the cross section of the position A-A in FIG. 10A to which bellows, drain spaces, metering channels, injection channels, and sample well air vent channels are added.
Figure 11:
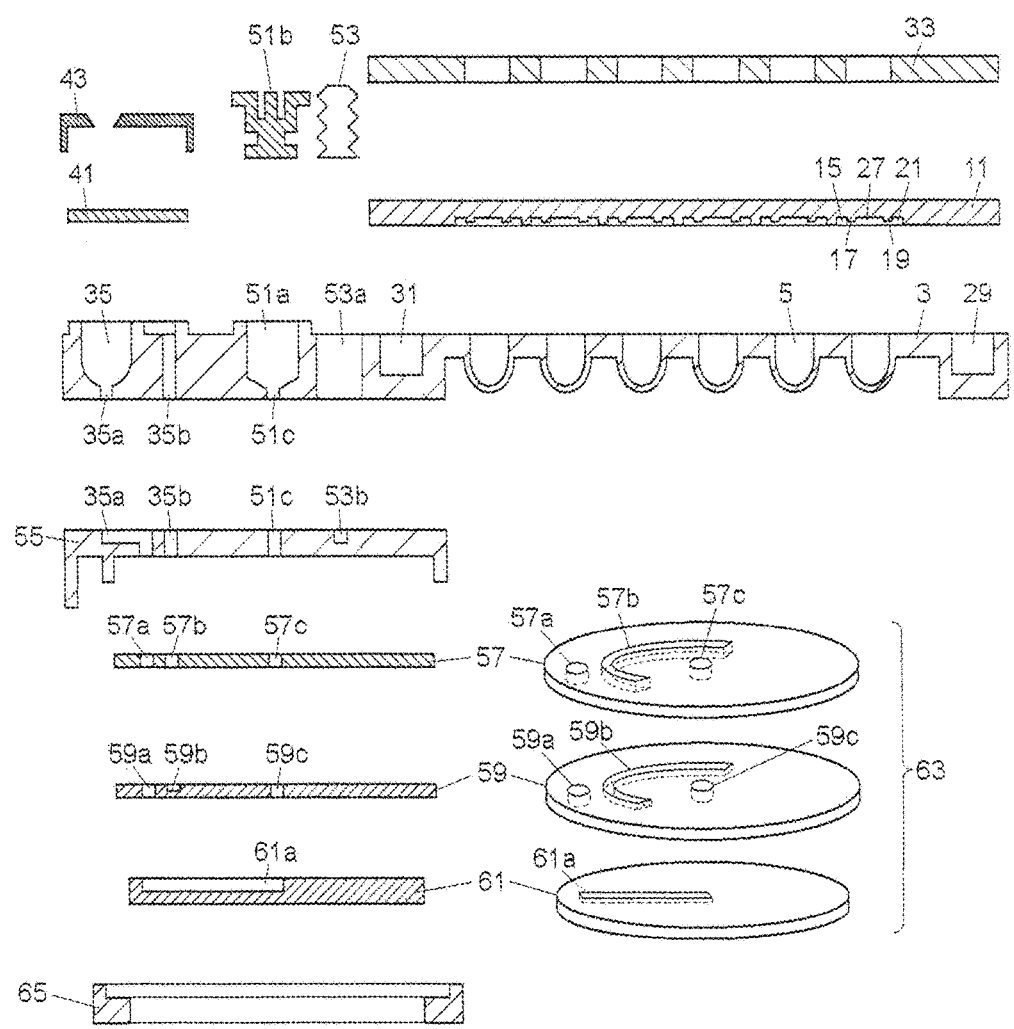
FIG. 11 presents an exploded sectional view of the example and a schematic exploded perspective view of a switching valve.
Figure 12A:
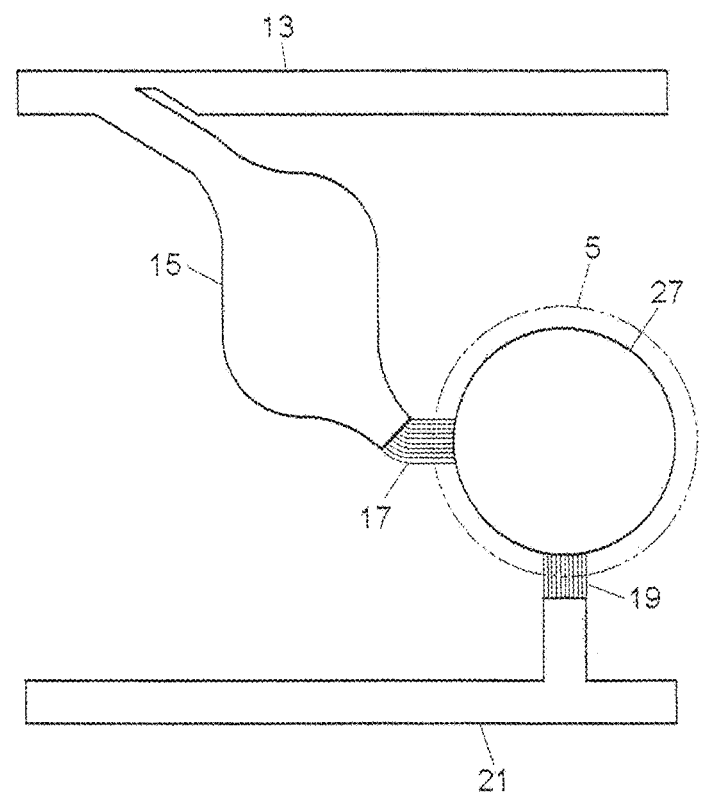
FIG. 12A is a schematic plan view showing the vicinity of one reaction well of the example.
Figure 12B:
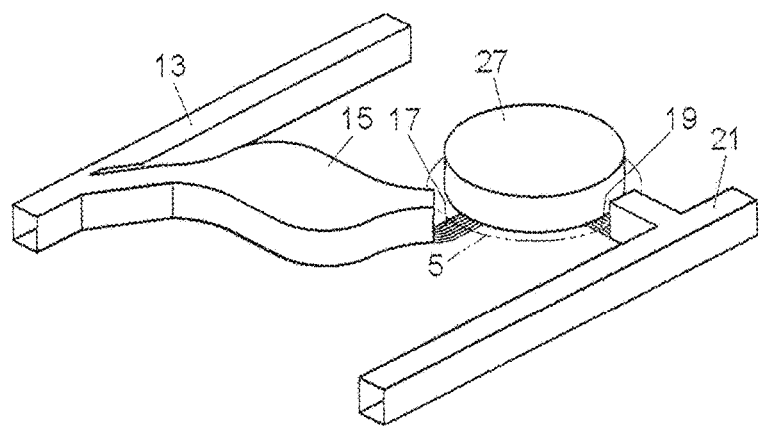
FIG. 12B is a schematic perspective view showing the vicinity of one reaction well of the example.
Figure 12C:
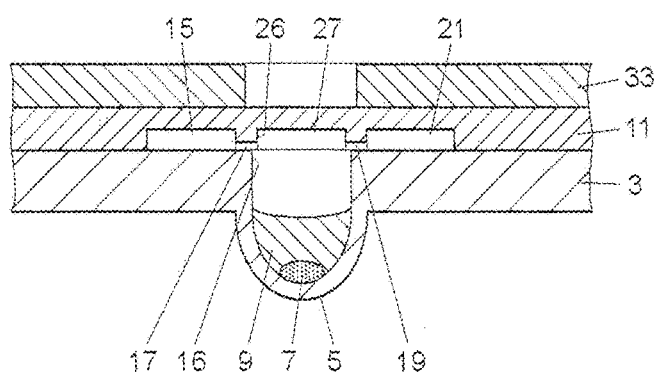
FIG. 12C is a schematic sectional view showing the vicinity of one reaction well of the example.
Figure 13A:
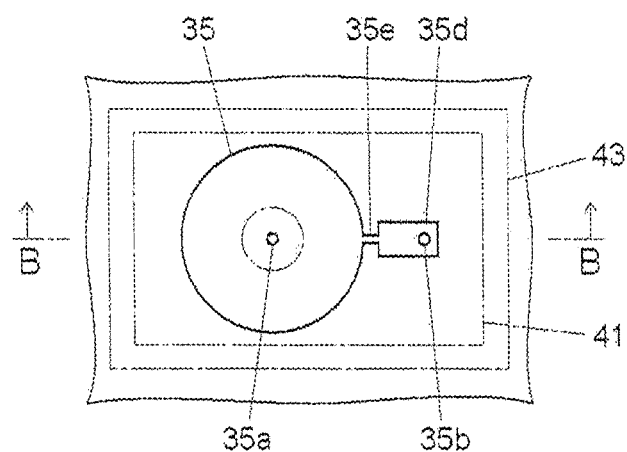
FIG. 13A is an enlarged plan view of a sample well of the example.
Figure 13B:
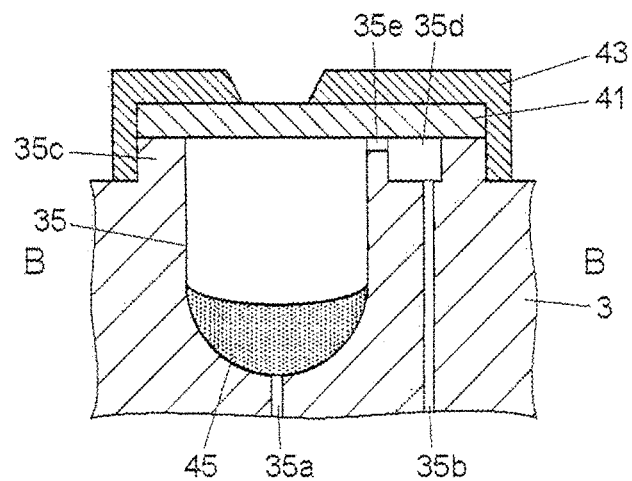
FIG. 13B is an enlarged view of a sample well of the example and is a sectional view at the position B-B of FIG. 13A.
Figure 14A:
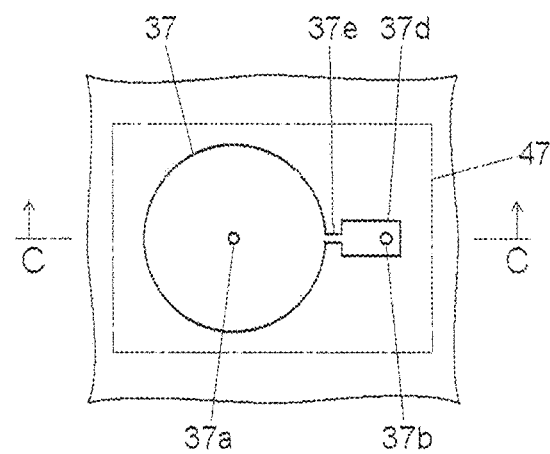
FIG. 14A is an enlarged plan view of a reagent well of the example.
Figure 14B:
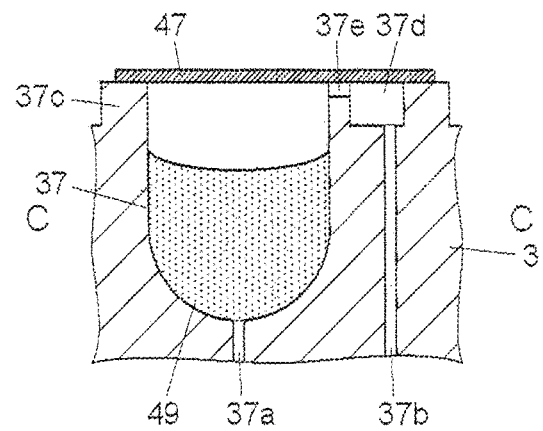
FIG. 14B is an enlarged view of a reagent well of the example and is a sectional view at the position C-C of FIG. 14A.
Figure 15A:
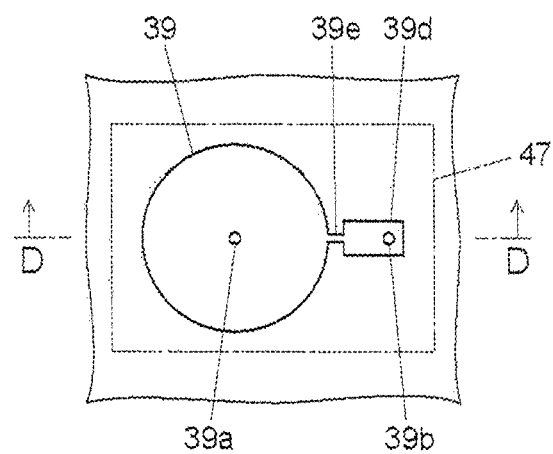
FIG. 15A is an enlarged plan view of a well for air suction of the example.
Figure 15B:
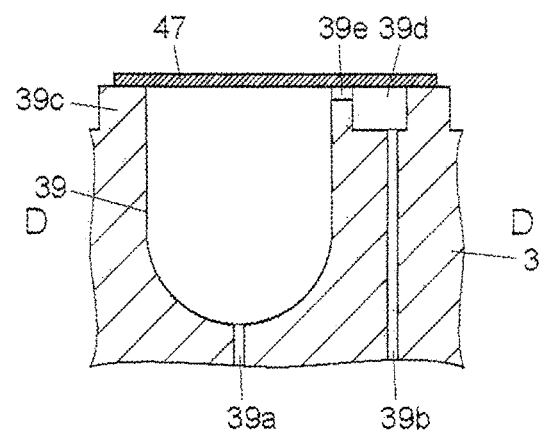
FIG. 15B is an enlarged view of a well for air suction of the example and is a sectional view at the position D-D of FIG. 15A.

FIG. 10A is a schematic plan view of one embodiment of a micro droplet operation device according to the present invention, and FIG. 10B is a schematic sectional view taken along the A-A line in FIG. 10A, which further includes the sectional views of a metering channel 15, an injection channel 17, reaction well air vent channels 19 and 21, a liquid drain space 29, an air drain space 31, and a bellows 53. FIG. 11 shows an exploded sectional view of the micro droplet operation device in the embodiment shown in FIG. 10A and a schematic exploded perspective view of a switching valve. FIGS. 12A to 12C are schematic plan view, schematic perspective view, and schematic sectional view of one reaction well of the micro droplet operation device in the embodiment shown in FIG. 10A and its vicinity, respectively. FIG. 13A is an expanded plan view of a sample well, and FIG. 13B is a sectional view taken along the B-B line in FIG. 13A. FIG. 14A is an expanded plan view of a reagent well, and FIG. 14B is a sectional view taken along the C-C line in FIG. 14A. FIG. 15A is an expanded plan view of a well for air suction, and FIG. 15B is a sectional view taken along the D-D line in FIG. 15A. With reference to these drawings, the micro droplet operation device according to one embodiment of the present invention will be described.

A micro droplet operation device 1 includes a plurality of reaction wells 5 each having an opening in one surface of a well base 3. In the micro droplet operation device 1 according to this embodiment of the present invention, the reaction wells 5 are arranged in an array of 6 rows and 6 columns in a staggered format. In each of the reaction wells 5, a reagent 7 and a wax 9 are contained.

The material of the well base 3 including the reaction wells 5 is not particularly limited. However, in a case where the micro droplet operation device 1 is intended to be disposable, the material of the well base 3 is preferably a cheaply-available material. Preferred examples of such a material include resin materials such as polypropylene and polycarbonate. In a case where the micro droplet operation device 1 is intended to be used to detect a substance in the reaction well 5 by absorbance, fluorescence, chemiluminescence, or bioluminescence, the container base 3 is preferably made of an optically-transparent resin so that optical detection can be carried out from the bottom of the reaction well 5. Particularly, in a case where the micro droplet operation device 1 is intended to be used for fluorescence detection, the container base 3 is preferably made of a low self-fluorescent (i.e., fluorescence emitted from a material itself is weak) and optically-transparent resin, such as polycarbonate. The thickness of the well base 3 is in a range of 0.2 to 4.0 mm, preferably in a range of 1.0 to 2.0 mm. From the viewpoint of low self-fluorescence, the thickness of the well base 3 for fluorescence detection is preferably small.

Referring to FIGS. 10A, 10B and FIGS. 12A to 12C, a channel base 11 is provided on the well base 3 so as to cover a region where the reaction wells 5 are arranged. The channel base 11 is made of, for example, PDMS (polydimethylsiloxane) or silicone rubber. The thickness of the channel base 11 is, for example, from 1.0 to 5.0 mm. The channel base 11 has a groove in its surface which is in contact with the well base 3. The groove and the surface of the well base 3 together form a main channel 13, the metering channel 15, the injection channel 17, the reaction well air vent channels 19 and 21, and drain space air vent channels 23 and 25. The main channel 13, the metering channel 15, and the injection channel 17 constitute a liquid introduction channel. In the surface of the channel base 11 which is in contact with the well base 3, a recess 27 is also provided so as to be located above each of the reaction wells 5. It is noted that, in FIG. 10A and FIGS. 12A and 12B, the channel base 11 is not shown, and only the groove and recess provided in the channel base 11 are shown.

The main channel 13 is constituted from one channel, and is therefore bent so as to run in the vicinity of all the reaction wells 5. One end of the main channel 13 is connected to a channel 13a constituted from a through hole provided in the well base 3. The channel 13a is connected to a port of a switching valve 63 (which will be described later). The other end of the main channel 13 is connected to the liquid drain space 29 provided in the well base 3. The main channel 13 is constituted from a groove having a depth of, for example, 400 μm (micrometers) and a width of, for example, 500 μm. It is noted that a part of the main channel 13 having a predetermined length (e.g., 250 μm) and located downstream of a position, to which the metering channel 15 is connected, has a width smaller than that of the other part of the main channel 13, and the width of such a part is, for example, 250 μm.

The metering channel 15 branches off the main channel 13, and is provided for each of the reaction wells 5. The end of the metering channel 15 on the opposite side from the main channel 13 is located in the vicinity of the reaction well 5. The depth of a groove constituting the metering channel 15 is, for example, 400 μm. The metering channel 15 is designed to have a predetermined internal capacity of, for example, 2.5 μL (microliters). A part of the metering channel 15 connected to the main channel 13 has a width larger than that of the above-described narrow part of the main channel 13 (e.g., 500 μm). Therefore, at a position where the metering channel 15 branches off the main channel 13, the resistance to the flow of a liquid coming from one end of the main channel 13 is larger in the main channel 13 than in the metering channel 15. For this reason, the liquid coming from one end of the main channel 13 first flows into the metering channel 15 to fill the metering channel 15, and then flows downstream through the narrow part of the main channel 13.

The injection channel 17 is also provided for each of the reaction wells 5. One end of the injection channel 17 is connected to the metering channel 15, and the other end of the injection channel 17 is connected to the recess 27 located above the reaction well 5 so as to be led to the space above the reaction well 5. The injection channel 17 is designed to have a size allowing the liquid-tightness of the reaction well 5 to be maintained in a state where there is no difference between the pressure in the reaction well 5 and the pressure in the injection channel 17. According to the present embodiment, the injection channel 17 is constituted from a plurality of grooves, and each groove has a depth of, for example, 10 μm and a width of, for example, 20 μm, and the pitch between the adjacent grooves is, for example, 20 μm, and the thirteen grooves are provided in a region having a width of 500 μm. In this case, the area of an interface between the groove constituting the injection channel 17 and the metering channel 15, that is, the cross-sectional area of the groove constituting the injection channel 17 is 200 μm². The recess 27 has a depth of, for example, 400 μm, and has a circular planar shape smaller than that of the reaction well 5.

The diameter of the recess 27 is smaller than the diameter of the reaction well 5 and the shoulder part 26 of the recess 27 is placed closer to the center of the reaction well 5 than the shoulder part 16 of the reaction well 5 is. This facilitates the liquid sample to fall into the reaction well 5.

The reaction well air vent channel 19 is provided for each of the reaction wells 5. One end of the reaction well air vent channel 19 is connected to the recess 27, which is located above the reaction well 5, at a position different from the position, to which the injection channel 17 is connected, so as to be located above the reaction well 5. The reaction well air vent channel 19 is designed to have a size allowing the liquid-tightness of the reaction well 5 to be maintained in a state where there is no difference between the pressure in the reaction well 5 and the pressure in the reaction well air vent channel 19. The other end of the reaction well air vent channel 19 is connected to the reaction well air vent channel 21. According to the present embodiment, the reaction well air vent channel 19 is constituted from a plurality of grooves, and each groove has a depth of, for example, 10 μm and a width of, for example, 20 μm, and the pitch between the adjacent grooves is, for example, 20 μm, and the thirteen grooves are provided in a region having a width of 500 μm.

The present embodiment has the plurality of reaction well air vent channels 21. To each of the reaction well air vent channels 21, the plurality of reaction well air vent channels 19 are connected. These reaction well air vent channels 21 are provided to connect the reaction well air vent channels 19 to the air drain space 31 provided in the well base 3. Each of the reaction well air vent channels 21 is constituted from a groove having a depth of, for example, 400 μm and a width of, for example, 500 μm.

The drain space air vent channel 23 is provided to connect the liquid drain space 29 to a port of the switching valve 63 (which will be described later). One end of the drain space air vent channel 23 is located above the liquid drain space 29. The other end of the drain space air vent channel 23 is connected to a channel 23a constituted from a through hole provided in the well base 3. The channel 23a is connected to a port of the switching valve 63 (which will be described later). The drain space air vent channel 23 is constituted from a groove having a depth of, for example, 400 μm and a width of, for example, 500 μm.

The drain space air vent channel 25 is provided to connect the air drain space 31 to a port of the switching valve 63 (which will be described later). One end of the drain space air vent channel 25 is located above the air drain space 31. The other end of the drain space air vent channel 25 is connected to a channel 25a constituted from a through hole provided in the well base 3. The channel 25a is connected to a port of the switching valve 63 (which will be described later). The drain space air vent channel 25 is constituted from a groove having a depth of, for example, 400 μm and a width of, for example, 500 μm.

On the channel base 11, a channel cover 33 (not shown in FIG. 1A) is provided. The channel cover 33 is provided to fix the channel base 11 to the well base 3. The channel cover 33 has a through hole formed to be located above each of the reaction wells 5.

Referring to FIGS. 10A, 10B and FIGS. 13A and 13B, in the well base 3, a sample well 35, a reagent well 37, and a well 39 for air suction are provided at positions other than the positions of a region where the reaction wells 5 are arranged, and the drain spaces 29 and 31. The sample well 35, the reagent well 37, and the well 39 for air suction constitute sealed wells of the micro droplet operation device according to the present invention.

In the well base 3, a sample channel 35a constituted from a through hole extending from the bottom of the sample well 35 to the back surface of the well base 3 and a sample well air vent channel 35b constituted from a through hole extending from the top surface to the back surface of the well base 3 are provided in the vicinity of the sample well 35. On the well base 3, a projecting portion 35c is provided so as to surround an opening of the sample well 35. In the projecting portion 35c, a sample well air vent channel 35d constituted from a through hole is provided so as to be located above the sample well air vent channel 35b. In the surface of the projecting portion 35c, a sample well air vent channel 35e which allows the sample well 35 to communicate with the sample well air vent channel 35d is provided.

The sample well air vent channel 35e is constituted from one or more narrow holes, and each narrow hole has a width of, for example, 5 to 200 µm and a depth of, for example, 5 to 200 µm. The sample well air vent channel 35e is provided to maintain the liquid-tightness of the sample well 35 in a state where there is no difference between the pressure in the sample well 35 and the pressure in the sample well air vent channel 35d. On the projecting portion 35c, a septum 41 as an elastic member to cover the sample well 35 and the air vent channel 35d is provided. The septum 41 is made of an elastic material such as silicone rubber or PDMS. Therefore, a dispensing device having a sharp tip can pass through the septum 41 to form a through hole, but the through hole can be closed by pulling the dispensing device out of the septum 41 due to its elasticity. On the septum 41, a septum stopper 43 for fixing the septum 41 is provided. The septum stopper 43 has an opening located above the sample well 35. According to the present embodiment, a reagent 45 is previously contained in the sample well 35.

As shown in FIGS. 14A and 14B, in the well base 3, a reagent channel 37a constituted from a through hole extending from the bottom of the reagent well 37 to the back surface of the well base 3 and a reagent well air vent channel 37b constituted from a through hole extending from the top surface to the back surface of the well base 3 are provided in the vicinity of the reagent well 37. On the well base 3, a projecting portion 37c is provided so as to surround an opening of the reagent well 37. In the projecting portion 37c, a reagent well air vent channel 37d constituted from a through hole is provided so as to be located above the reagent well air vent channel 37b. In the surface of the projecting portion 37c, a reagent well air vent channel 37e which allows the reagent well 37 to communicate with the reagent well air vent channel 37d is provided.

The reagent well air vent channel 37e is constituted from one or more narrow holes, and each narrow hole has a width of, for example, 5 to 200 µm and a depth of, for example, 5 to 200 µm. The reagent well air vent channel 37e is provided to maintain the liquid-tightness of the reagent well 37 in a state where there is no difference between the pressure in the reagent well 37 and the pressure in the reagent well air vent channel 37d. On the projecting portion 37c, a film 47 made of, for example, aluminum to cover the reagent well 37 and the air vent channel 37d is provided. In the reagent well 37, dilution water 49 is contained.

As shown in FIGS. 15A and 15B, the well 39 for air suction has the same structure as the reagent well 37. That is, in the well base 3, a channel 39a for air suction constituted from a through hole extending from the bottom of the well 39 for air suction to the back surface of the well base 3 and an air vent channel 39b for the well for air suction constituted from a through hole extending from the top surface to the back surface of the well base 3 are provided in the vicinity of the well 39 for air suction. On the well base 3, a projecting portion 39c having air vent channels 39d and 39e for the well for air suction is provided so as to surround an opening of the well 39 for air suction. On the projecting portion 39c, a film 47 made of, for example, aluminum is provided. The well 39 for air suction contains neither a liquid nor a solid, but is filled with air.

Referring to FIGS. 10A, 10B and FIG. 12, in the surface of the well base 3, a syringe 51 is provided at a position other than positions of a region where the reaction wells 5 are arranged, the drain spaces 29 and 31, and the wells 35, 37, and 39. The syringe 51 is constituted from a cylinder 51a formed in the well base 3 and a plunger 51b placed in the cylinder 51a. In the well base 3, a syringe channel 51c constituted from a through hole extending from the bottom of the cylinder 51a to the back surface of the well base 3 is provided.

In the well base 3, the bellows 53 is also provided at a position other than the positions of a region where the reaction wells 5 are arranged, the drain spaces 29 and 31, the wells 35, 37 and 39, and the syringe 51. The bellows 53 expands and contracts, and therefore the internal capacity of the bellows 53 is passively variable. The bellows 53 is placed in, for example, a through hole 53a provided in the well base 3.

Further, a well bottom 55 is attached to the back surface of the well base 3 at a position other than the position of a region where the reaction wells 5 are arranged. In the well bottom 55, an air vent channel 53b is provided at a position allowing the air vent channel 53b to communicate with the bellows 53. The bellows 53 is connected to the well bottom 55 so as to be in close contact with the surface of the well bottom 55. The well bottom 55 is provided to guide the channels 13a, 23a, 25a, 35a, 35b, 37a, 37b, 39a, 39b, 51c, and 53b to predetermined port positions.

On the surface of the reaction well bottom 55 located on the opposite side from the well base 3, the rotary switching valve 63 is provided. The switching valve 63 is constituted from disk-shaped sealing plate 57, rotor upper 59, and rotor base 61. The switching valve 63 is attached to the well bottom 55 by means of a lock 65.

The sealing plate 57 has a through hole 57a, a through groove 57b, and a through hole 57c. The through hole 57a is provided in the vicinity of the peripheral portion of the sealing plate 57, and is connected to any one of the channels 13a, 35a, 37a, and 39a. The through groove 57b is provided inside the through hole 57a and on a circle concentric with the sealing plate 57, and is connected to at least two of the channels 23a, 25a, 35b, 37b, 39b, and 53b. The through hole 57c is provided at the center of the sealing plate 57, and is connected to the syringe channel 51c.

The rotor upper 59 has a through hole 59a, a groove 59b, and a through hole 59c. The through hole 59a is provided at a position corresponding to the through hole 57a provided in the sealing plate 57. The groove 59b is provided in the surface of the rotor upper 59 so as to correspond to the through groove 57b provided in the sealing plate 57. The through hole 59c is provided at the center of the rotor upper 59.

The rotor base 61 has a groove 61*a*. The groove 61*a* is provided in the surface of the rotor base 61 to connect the through hole 59*a* provided in the peripheral portion of the rotor upper 59 and the through hole 59*c* provided at the center of the rotor upper 59 to each other.

By rotating the switching valve 63, the syringe channel 51*c* is connected to any one of the channels 13*a*, 35*a*, 37*a*, and 39*a*, and at the same time, the air vent channel 53*b* is also connected to at least any one of the channels 23*a*, 25*a*, 35*b*, 37*b*, and 39*b*.

The switching valve 63 shown in FIG. 10A is in its initial state where the syringe channel 51*c* is not connected to any one of the channels 13*a*, 35*a*, 37*a*, and 39*a*, and the air vent channel 53*b* is not connected to any one of the channels 23*a*, 25*a*, 35*b*, 37*b*, and 39*b*, either.

As described above, the injection channel 17 provided in the micro droplet operation device 1 is designed so that the liquid-tightness of the reaction well 5 is maintained in a state where there is no difference between the pressure in the injection channel 17 and the pressure in the reaction well 5. The reaction well air vent channel 19 is also designed so that the liquid-tightness of the reaction well 5 is maintained in a state where there is no difference between the pressure in the reaction well 5 and the pressure in the reaction well air vent channel 19. The main channel 13 constituting the liquid introduction channel, the liquid drain space 29 connected to the main channel 13, and the drain space air vent channel 23 can be hermetically sealed by switching of the switching valve 63. The wells 35, 37, and 39 are sealed with the septum 41 or the film 47. The channels 35*a*, 35*b*, 37*a*, 37*b*, 39*a*, and 39*b* connected to the wells 35, 37, and 39, respectively, can be hermetically sealed by switching the switching valve 63. One end of the air vent channel 53*b* is connected to the bellows 53 and therefore the air vent channel 53*b* is hermetically sealed. As described above, the wells and channels in the micro droplet operation device 1 constitute a closed system. It is noted that even in a case where the micro droplet operation device 1 does not have the bellows 53 and the air vent channel 53*b* is connected to the atmosphere outside the micro droplet operation device 1, the air vent channel 53*b* can be cut off from the wells and the channels other than the air vent channel 53*b* provided in the micro droplet operation device 1 by switching of the switching valve 63, and therefore the wells for containing a liquid and the channels for flowing a liquid can be hermetically sealed.

Figure 16:
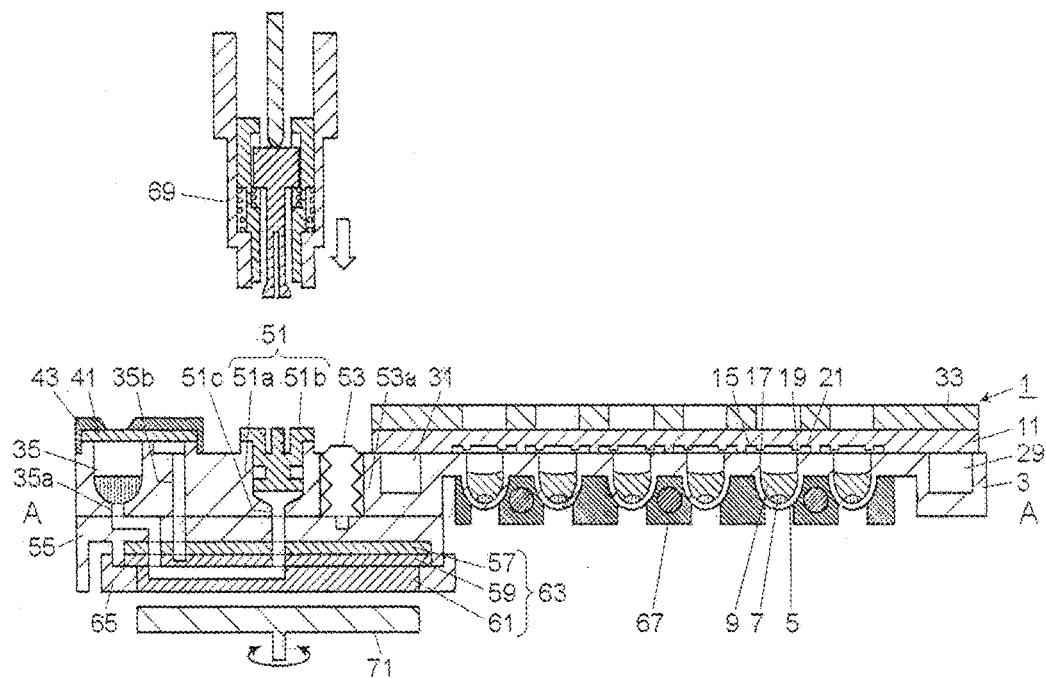
FIG. 16 is a schematic sectional view showing a reaction processing apparatus for processing a micro droplet operation device together with a micro droplet operation device.

FIG. 16 is a sectional view showing the micro droplet operation device 1 shown in FIGS. 10A and 10B and a reaction processing apparatus for processing the micro droplet operation device 1. The micro droplet operation device 1 shown in FIG. 16 has the same structure as that shown in FIG. 10, and therefore the description thereof is omitted.

The reaction processing apparatus includes a temperature control system 67 for controlling the temperature of the reaction wells 5, a syringe driving unit 69 for driving the syringe 51, and a switching valve driving unit 71 for switching the switching valve 63.

FIGS. 17 to 23 are plan views for explaining the operation of introducing a sample liquid into the reaction wells 5 from the sample well 35. This operation will be described with reference to FIGS. 10A, 10B and FIGS. 17 to 23.

A dispensing device having a sharp tip (not shown) is prepared, and the dispensing device is passed through the septum 41 provided on the sample well 35 to dispense, for example, 5 µL of a sample liquid into the sample well 35. After the completion of the dispensing of the sample liquid, the dispensing device is pulled out of the septum 41. By pulling the dispensing device out of the septum 41, a through hole formed in the septum 41 is closed due to the elasticity of the septum 41.

The syringe driving unit 69 is connected to the plunger 51*b* of the syringe 51, and the switching valve driving unit 71 is connected to the switching valve 63.

Figure 17:
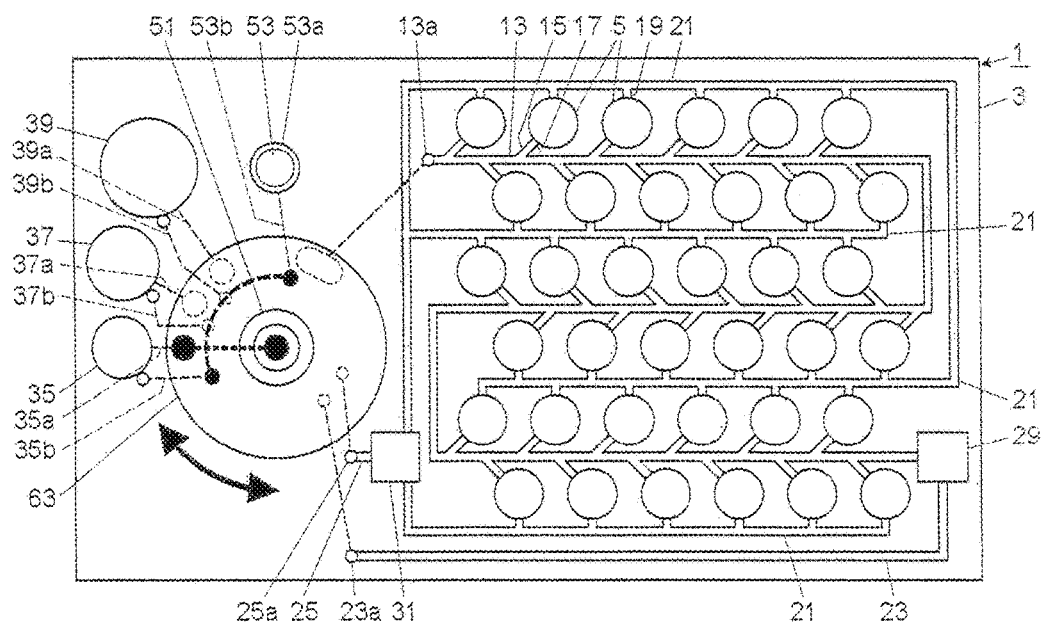
FIG. 17 is a plan view illustrating the operation of introducing a sample liquid from a sample container into a reaction well.

As shown in FIG. 17, the switching valve 63 in its initial state shown in FIG. 10A is rotated to connect the syringe channel 51*c* to the sample channel 35*a* and to connect the air vent channel 53*b* to the sample well air vent channel 35*b*. At this time, the air vent channels 37*b* and 39*b* are also connected to the air vent channel 53*b*. The sample well 35 contains, for example, 45 µL of a reagent 45.

The syringe 51 is slidably moved to mix the sample liquid and the reagent 45 contained in the sample well 35. Then, for example, only 10 µL of the mixture contained in the sample well 35 is sucked into the channel in the switching valve 63, the syringe channel 51*c*, and the syringe 51. At this time, the bellows 53 expands and contracts with changes in the volume of a gas contained in the sample well 35, since the sample well 35 is connected to the bellows 53 through the air vent channels 35*e*, 35*d*, and 35*b*, the switching valve 63, and the air vent channel 53*b*.

Figure 18:
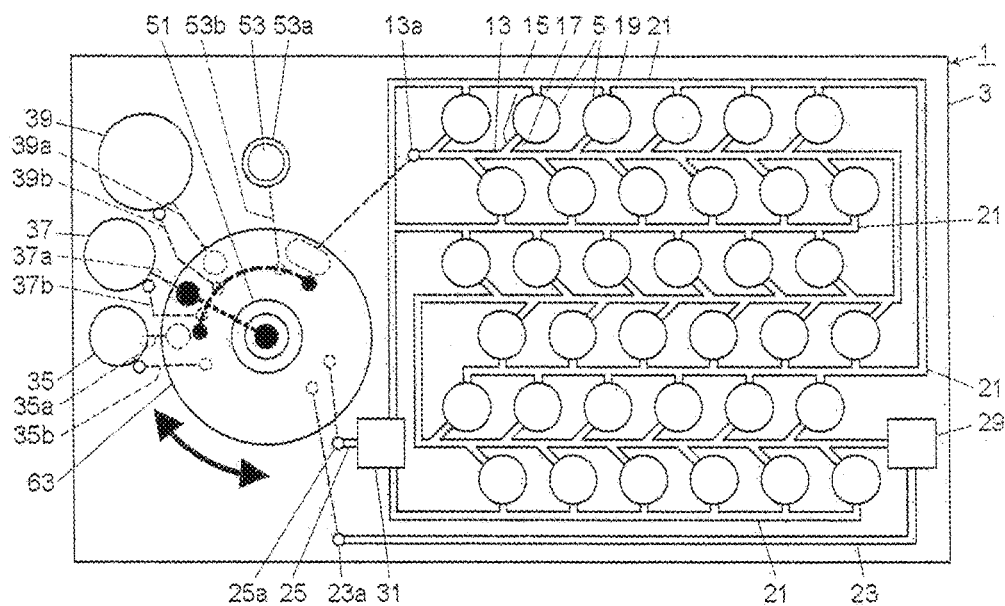
FIG. 18 is a plan view illustrating the operation following the operation in FIG. 17.

As shown in FIG. 18, the switching valve 63 is rotated to connect the syringe channel 51*c* to the reagent channel 37*a* and to connect the air vent channel 53*b* to the reagent well air vent channel 37*b*. The reagent well 37 contains, for example, 190 µL of dilution water 49. The mixture sucked into the channel in the switching valve 63, the syringe channel 51*c*, and the syringe 51 is injected into the reagent well 37. Then, the syringe 51 is slidably moved to mix the mixture and the dilution water 49. For example, the whole diluted mixture, that is, 200 µL of the diluted mixture is sucked into the channel in the switching valve 63, the syringe channel 51*c*, and the syringe 51. At this time, the bellows 53 expands and contracts with changes in the volume of a gas contained in the reagent well 37, since the reagent well 37 is connected to the bellows 53 through the air drain channels 37*e*, 37*d*, and 37*b*, the switching valve 63, and the air vent channel 53*b*.

Figure 19:
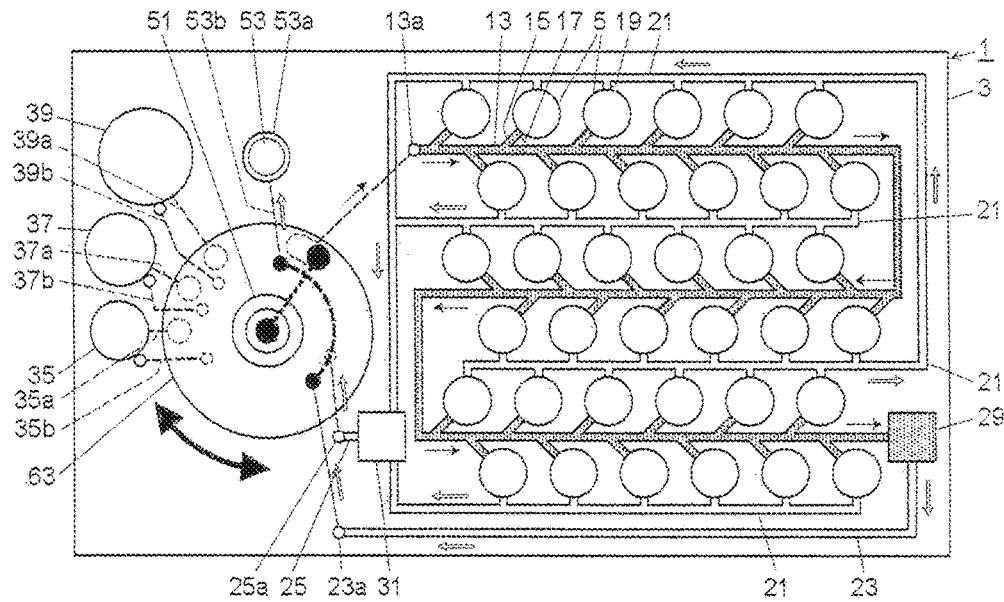
FIG. 19 is a plan view illustrating the operation following the operation in FIG. 18.

As shown in FIG. 19, the switching valve 63 is rotated to connect the syringe channel 51*c* to the channel 13*a* connected to one end of the main channel 13 and to connect the air vent channel 53*b* to the channels 23*a* and 25*a* connected to the liquid drain space 29 and the air drain space 31, respectively. The syringe 51 is driven in an extrusion direction to send the diluted mixture sucked into the channel in the switching valve 63, the syringe channel 51*c*, and the syringe 51 to the main channel 13. As shown by the arrows and dots in FIG. 10, the diluted mixture injected into the main channel 13 through the channel 13*a* fills the metering channels 15 one after another in order of increasing distance from the channel 13*a*, and then reaches the liquid drain space 29. The injection channel 17 allows the passage of a gas but does not allow the passage of the diluted mixture at an introduction pressure applied to introduce the diluted mixture into the main channel 13 and the metering channels 15. When the diluted mixture is introduced into the metering channel 15, a gas contained in the metering channel 15 is transferred into the reaction well 5 through the injection channel 17. Due to the transfer of the gas into the reaction well 5, a gas contained in the reaction well 5 is partially transferred into the reaction well air vent channels 19 and 21. Furthermore, a gas contained in the channels between the reaction well air vent channel 19 and the bellows 53 is sequentially moved toward the bellows 53 (see open arrows in FIG. 10). Further, due to the injection of the diluted mixture into the liquid drain space 29, a gas contained in the channels between the liquid drain space 29 and the bellows 53 is sequentially moved toward the bellows 53 (see open arrows in FIG. 10). As a result, the bellows 53 expands.

Figure 20:
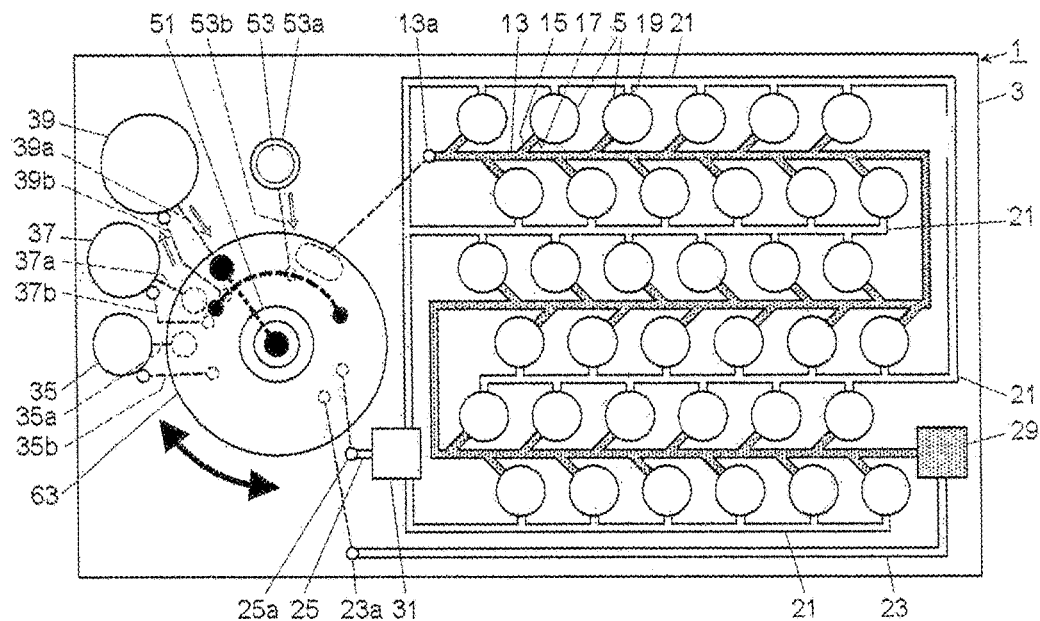
FIG. 20 is a plan view illustrating the operation following the operation in FIG. 19.

As shown in FIG. 20, the switching valve 63 is rotated to connect the syringe channel 51c to the channel 39a for air suction and to connect the air vent channel 53b to the air vent channel 39b for the well for air suction. Then, the syringe 51 is driven in a suction direction to suck a gas contained in the well 39 for air suction into the channel in the switching valve 63, the syringe channel 51c, and the syringe 51. At this time, the bellows 53 contracts due to the decompression of the well 39 for air suction (see open arrows in FIG. 11), since the well 39 for air suction is connected to the bellows 53 through the air vent channels 39e, 39d, and 39b, the switching valve 63, and the air vent channel 53b.

Figure 21:
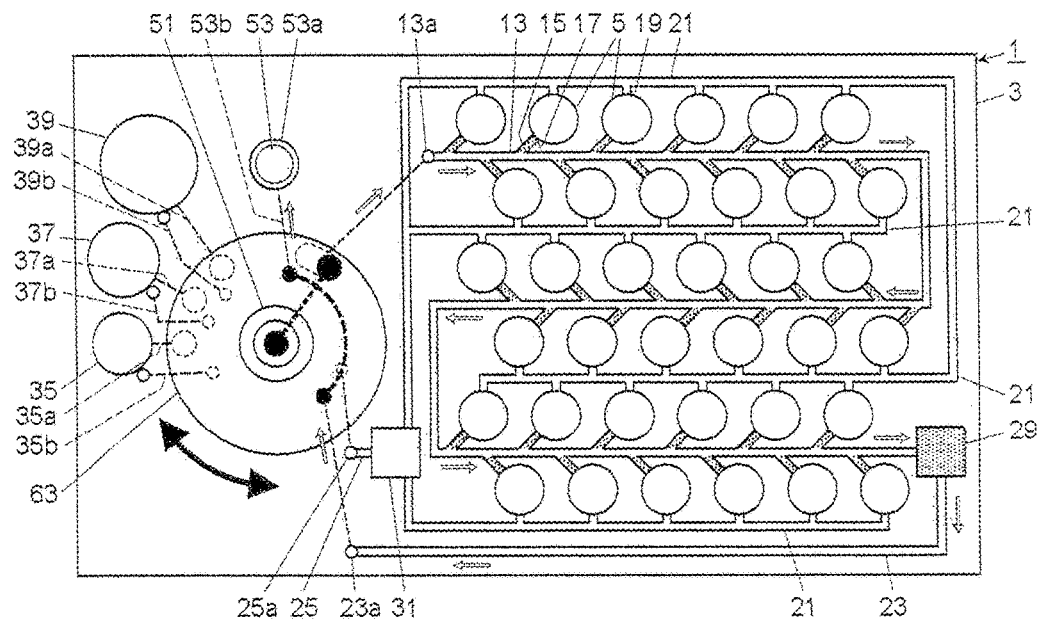
FIG. 21 is a plan view illustrating the operation following the operation in FIG. 20.

As shown in FIG. 21, the switching valve 63 is rotated to connect the syringe channel 51c to the channel 13a and to connect the air vent channel 53b to the channels 23a and 25a as in the case of a connection state shown in FIG. 19. Then, the syringe 51 is driven in an extrusion direction to send a gas contained in the channel in the switching valve 63, the syringe channel 51c, and the syringe 51 into the main channel 13 to purge the diluted mixture from the main channel 13 (see open arrows in FIG. 12). At this time, the diluted mixture remains in the metering channels 15 (see dots in FIG. 12) because the injection channels 17 do not allow the passage of the diluted mixture at a purge pressure applied to purge the diluted mixture from the main channel 13. The purged diluted mixture is injected into the liquid drain space 29. Further, due to the injection of the diluted mixture into the liquid drain space 29, a gas contained in the channels between the liquid drain space 29 and the bellows 53 is sequentially moved toward the bellows 53 (see open arrows in FIG. 12). As a result, the bellows 53 expands.

Figure 22:
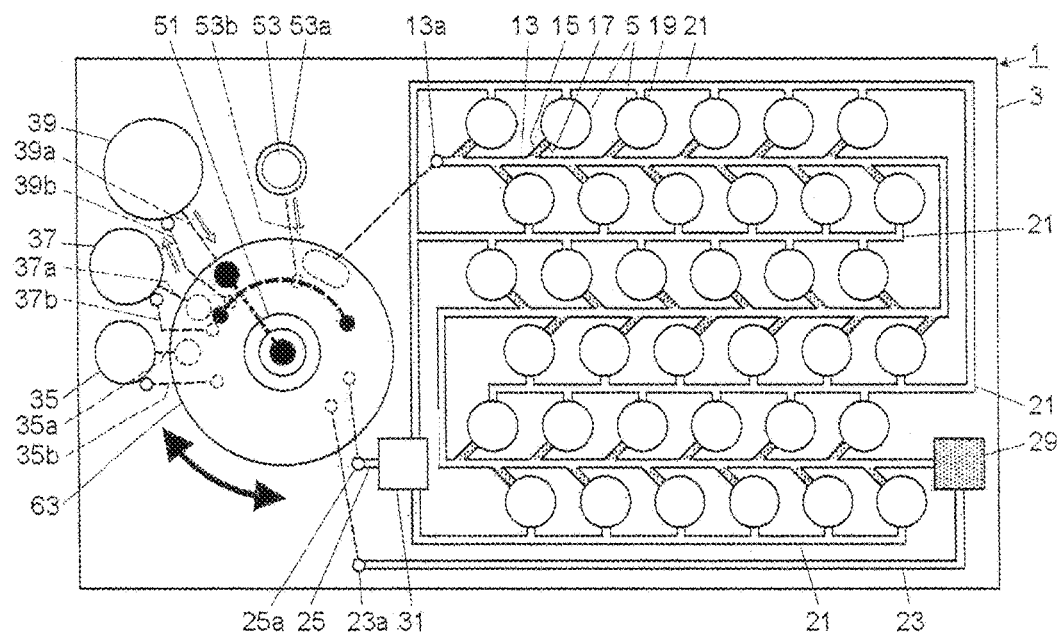
FIG. 22 is a plan view illustrating the operation following the operation in FIG. 21.

As shown in FIG. 22, the switching valve 63 is rotated to connect the syringe channel 51c to the channel 39a for air suction and to connect the air vent channel 53b to the air vent channel 39b for the well for air suction as in the case of a connection state shown in FIG. 20. Then, the syringe 51 is driven in a suction direction to suck a gas contained in the well 39 for air suction into the channel in the switching valve 63, the syringe channel 51c, and the syringe 51. At this time, as in the case described with reference to FIG. 20, the bellows 53 contracts (see open arrows in FIG. 22).

Figure 23:
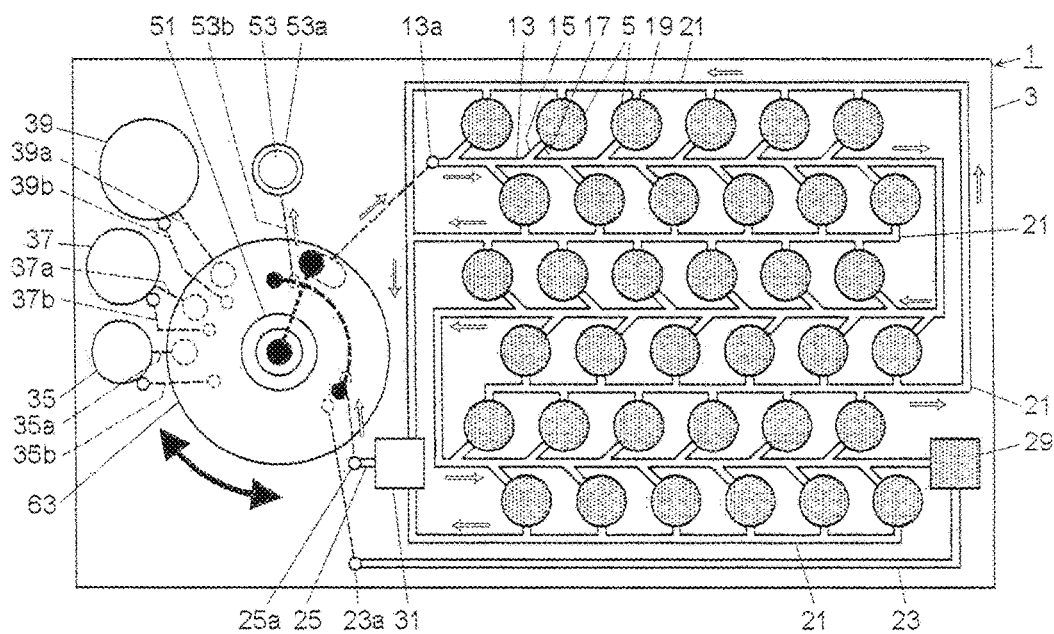
FIG. 23 is a plan view illustrating the operation following the operation in FIG. 22.

As shown in FIG. 23, the switching valve 63 is rotated to connect the syringe channel 51c to the channel 13a and to connect the air vent channel 53b to the channel 25a. It is noted that the connection state shown in FIG. 14 is different from those shown in FIGS. 19 and 21 in that the liquid drain space 29, to which the downstream end of the main channel 13 is connected, is not connected to the channel in the switching valve 63. Then, the syringe 51 is driven in an extrusion direction. Since the downstream end of the main channel 13 is not connected to the bellows 53, a pressure larger than the liquid introduction pressure and the purge pressure is applied to the inside of the main channel 13. As a result, the diluted mixture in the metering channels 15 is injected into the reaction wells 5 through the injection channels 17.

In this case, in the connection part of the reaction well 5 and the injection channel 17, the shoulder part 26 of the recess 27 is disposed closer to the center of the reaction well than the shoulder part 16 of the reaction well 5 is, whereby the liquid droplet injected from the injection channel 17 hardly sticks to the ceiling (part of the channel base 11 disposed opposite to the reaction well 5) and is facilitated to fall into the reaction well 5 by its own weight.

After the completion of the injection of the diluted mixture into the reaction wells 5, a gas contained in the main channel 13 is partially flown into the reaction wells 5 through the metering channels 15 and the injection channels 17. At this time, a gas contained in the channels between the reaction wells 5 and the bellows 53 is sequentially moved toward the bellows 53 (see open arrows in FIG. 14), since the reaction wells 5 are connected to the bellows 53 through the reaction well air vent channels 19 and 21, the air drain space 31, the drain space air vent channel 25a, and the air vent channel 53b. As a result, the bellows 53 expands.

The switching valve 63 is returned to its initial state shown in FIG. 10A to hermetically seal the wells, channels, and drain spaces provided in the micro droplet operation device 1. Then, the reaction wells 5 are heated by the temperature control system 67 to melt the wax 9. As a result, the diluted mixture injected into each of the reaction wells 5 sinks below the wax 9, and therefore the diluted mixture is mixed with the reagent 7 so that a reaction occurs. As described above, by using the micro droplet operation device 1, it is possible to perform reaction processing in a closed system.

In addition, before a diluted mixed solution is injected into the reaction well 5, the reaction well 5 may be heated by a temperature control mechanism 67 to melt the wax 9 in advance, and the wax 9 may be melted at the time of the injection of the diluted mixed solution into the reaction well 5. In this case, when the wall surface of the reaction well 5 is made wet with the wax having a contact angle less than 90° with the sidewall of the reaction well 5, the liquid sample is facilitated to flow along the sidewall within the reaction well.

Additionally, if a treatment is applied to the part opposite to the reaction well 5 of the channel base 11 so that the contact angle with the liquid droplet becomes 90° or larger, the liquid droplet injected into the reaction well 5 from the injection channel 17 repels at the part subjected to hydrophobic treatment and is facilitated to fall into the reaction well 5 by its own weight.

Then the diluted mixture injected into each of the reaction wells 5 immediately sinks below the wax 9, and is then mixed with the reagent 7 so that a reaction occurs. Even when the switching valve 63 is in the connection state shown in FIG. 23, the hermeticity of the micro droplet operation device 1 is maintained by the bellows 53. By returning the switching valve 63 to its initial state shown in FIG. 10A after the injection of the diluted mixture into the reaction wells 5, it is possible to hermetically seal the wells, channels, and the drain spaces provided in the micro droplet operation device 1. It is noted that the switching valve 63 may be returned to its initial state shown in FIGS. 10A and 10B at any timing during the period from just after the injection of the diluted mixture into the reaction wells 5 until the end of the reaction between the diluted mixture and the reagent 7, or may be returned to its initial state shown in FIG. 1 after the completion of the reaction between the diluted mixture and the reagent 7. As described above, by using the micro droplet operation device 1, it is possible to perform reaction processing in a closed system. In addition, it is also possible to maintain the hermeticity of the micro droplet operation device 1 before and after reaction processing.

According to the present embodiment, grooves for forming the channels 13, 15, 17, 19, 21, and 23 are provided in the channel base 11, but the present invention is not limited to this embodiment. For example, grooves for forming all or part of these channels may be provided in the surface of the well base 3.

As described above, since the reaction processing method according to the present invention is carried out using the micro droplet operation device according to the present invention including a reaction well 5, a liquid introduction channel 12*a* connected to the reaction well 5, and a reaction well air vent channel 19 connected to the reaction well 5, wherein the liquid introduction channel 12*a* is constituted from a groove formed in the contact surface between two bases 3, 11 bonded together or from the groove and a through hole formed in the bases 3, 11 and includes a main channel 13, a metering channel 15 branched off the main channel 13 and having a predetermined capacity, and an injection channel 17 whose one end is connected to the metering channel 15 and the other end is connected to the reaction well 5, and wherein the main channel 13 and the reaction well air vent channel 19 are hermetically sealed and the injection channel 17 is formed narrower than the metering channel 15 and does not allow the passage of a liquid at an introduction pressure applied to introduce the liquid into the main channel 13 and the metering channel 15 and at a purge pressure applied to purge the liquid from the main channel 13 but allows the passage of the liquid at a pressure higher than the introduction pressure and the purge pressure, it is possible to prevent the entry of foreign matter from the outside of the micro droplet operation device and the pollution of a surrounding environment with the liquid.

Since the micro droplet operation device according to the present invention has the reaction well air vent channel 19 connected to the reaction well 5, it is possible to move a gas between the reaction well 5 and the reaction well air vent channel 19 when a liquid is injected into the reaction well 5 through the injection channel, thereby making it possible to smoothly inject the liquid into the reaction well 5. The reaction well air vent channel 19 can also be used to suck a gas contained in the reaction well 5 to decompress the reaction well 5 to inject a liquid into the reaction well 5.

In the example 9, the bellows 53 connected to the air vent channel 53*b* may have another structure as long as it is a variable capacity member whose internal capacity is passively variable. Examples of such a bellows 53 having another structure include a bag-shaped one made of a flexible material and a syringe-shaped one.

The micro droplet operation device according to the present invention does not always need to have a variable capacity member such as a bellows 53. Further, in a case where a liquid such as a reagent is not previously contained in the well 35, 37, or 39, the air vent channel thereof does not always need to partially have the channel 35*e*, 37*e*, or 39*e* constituted from a narrow hole.

In the example 9, the air vent channels 35*b*, 37*b*, and 39*b*, which communicate with the wells 35, 37, and 39 provided as sealed wells, are connected to the air vent channel 53*b* through the switching valve 63, but may be directly connected to the outside of the micro droplet operation device or a variable capacity part such as a bellows 53. Further, each of the wells 35, 37, and 39 may be sealed by using an openable and closable cap.

In the example 9, the well base 3 is constituted from one component, but may be constituted from two or more components.

The reagent contained in the reaction well 5 may be a dry reagent. It is noted that the sample well 35 and the reaction well 5 do not always need to previously contain a reagent.

Further, in the example 9, the reagent well 37 contains dilution water 49, but may contain a reagent instead of the dilution water 49.

The well base 3 may further have a gene amplification well for carrying out gene amplification reaction. For example, the empty reagent well 37 may be used as a gene amplification well.

By previously placing a reagent for gene amplification reaction in the reaction well 5, it is possible to carry out gene amplification reaction in the reaction well 5. Further, in a case where a liquid to be introduced into the main channel 13 contains a gene, a probe which reacts with the gene may be previously placed in the reaction well 5.

In the example 9, the syringe 51 is placed on the switching valve 63. However, the position of the syringe 51 is not limited to a position on the switching valve 63, and the syringe 51 may be placed at any position.

The micro droplet operation device according to the present invention does not always need to have the syringe 51, and a syringe provided outside the micro droplet operation device may be used to discharge and suck a liquid or a gas.

In the example 9, the rotary switching valve 63 is used as a switching valve. However, a switching valve for use in the micro droplet operation device according to the present invention is not limited thereto, and various channel switching valves can be used. The micro droplet operation device according to the present invention may have a plurality of switching valves.

In the example 9, a liquid filling the metering channel 15 is injected into the reaction well 5 through the injection channel 17 by applying a pressure to the inside of the main channel 13 after air purge, but the reaction processing method according to the present invention is not limited to such a method. For example, a liquid filling the metering channel 15 may be injected into the reaction well 5 through the injection channel 17 by creating a negative pressure in the reaction well air vent channel 21 and then in the reaction well 5. In this case, it is necessary to change the channel configuration of the micro droplet operation device so that a negative pressure can be created in the reaction well air vent channel 21 by using the syringe 51. Alternatively, another syringe may be additionally prepared. In this case, a positive pressure is created in the main channel 13 and a negative pressure is created in the reaction well 5 to inject the liquid into the reaction well 5.

In the example 9, one main channel 13 is provided, and all the metering channels 15 are connected to the main channel 13. However, the channel configuration of the micro droplet operation device according to the present invention is not limited thereto. For example, a plurality of main channels may be provided. In this case, one or more metering channels may be connected to each of the main channels.

In the micro droplet operation device according to the present invention in which the liquid introduction channel includes the main channel, metering channel and the injection channel, in order to hermetically seal the main channel, the main channel may be hermetically sealed by, for example, allowing both ends of the main channel to be openable and closable. The phrase "allowing both ends of the main channel to be openable and closable" includes a case where each end of the main channel is connected to another space, and the end of the space located on the opposite side from the main channel is openable and closable. In the case of the example 9, such another space corresponds to, for example, the channel 13*a*, the liquid drain space 29, the drain space air vent channel 23, or the channel 23*a*.

Further, in the micro droplet operation device according to the present invention, in order to hermetically seal the reaction well air vent channel, the reaction well air vent channel may be hermetically sealed by, for example, allowing the end of the reaction well air vent channel located on the opposite side from the reaction well to be openable and closable. The phrase "allowing the end of the reaction well air vent channel located on the opposite side from the reaction well to be openable and closable" includes a case where the end of the reaction well air vent channel located on the opposite side from the reaction well is connected to another space, and the end of the space located on the opposite side from the reaction well air vent channel is openable and closable. In the case of the example 9, such another space corresponds to, for example, the air drain space 31, the drain space air vent channel 25, or the channel 25*a*.

In the case of such an aspect, a liquid is introduced into the main channel and the metering channels, and then the liquid is purged from the main channel, and then the liquid remaining in the metering channels is injected into the reaction wells, and then both ends of the main channel and one end of the reaction well air vent channel located on the opposite side from the reaction well are closed to hermetically seal the main channel and the reaction well air vent channel.

Although Example 9 was described using a microfluid operation device having the recess 27 disposed in the ceiling of the reaction well 5, Example 9 and any of or all of Examples 1 to 8 described above may be combined.

Although the present invention has been described above with reference to the various embodiments, the present invention is not limited to these embodiments. The shape, material, position, number, and size of each component and the channel configuration of the micro droplet operation device in the above description are merely examples, and various changes can be made without departing from the scope of the present invention defined in claims.

What is claimed is:
1. A micro droplet operation device comprising:
   a base plate;
   a well formed in the base plate and having an opening in one surface of the base plate;
   a cover plate covering the opening of the well and attached to the one surface of the base plate;
   a liquid introduction channel constituted from a groove formed in a contact surface between the base plate and the cover plate and connected to the well; and
   an air vent mechanism constituted from a groove formed in the contact surface separately from the liquid introduction channel and connected to the well at a position different from the liquid introduction channel, wherein
   a surface treatment liquid having a contact angle less than 90° with a sidewall of the well or a solid which becomes the surface treatment liquid when it dissolves is accommodated in the well so that the sidewall of the well is wetted with the surface treatment liquid, and
   a liquid introduced into the well is maintained in a droplet state by the surface treatment liquid.
2. The micro droplet operation device according to claim 1, wherein embossing, texturing, machining or groove machining is applied to the sidewall of the well in order to increase the surface area of the sidewall.
3. The micro droplet operation device according to claim 1,
   wherein the liquid introduction channel is constituted from a groove formed in the contact surface or from the groove and a through hole formed in the cover plate, the liquid introduction channel including a main channel, a metering channel of a predetermined capacity branched from the main channel, and an injection channel of which one end is connected to the metering channel and the other end is connected to the well, and
   wherein the injection channel is formed to have a higher inflow withstanding pressure than the metering channel so as to not pass a liquid in a liquid introduction pressure state when a liquid is introduced into the main channel and metering channel, and also in a purge pressure state when a liquid within the main channel is purged, but passes a liquid under higher pressures than those.

* * * * *